(12) United States Patent
Peliks et al.

(10) Patent No.: US 11,331,037 B2
(45) Date of Patent: May 17, 2022

(54) METHODS AND APPARATUS FOR DETERMINING THE INTEGRITY OF A BODILY CAVITY

(71) Applicant: AEGEA MEDICAL INC., Menlo Park, CA (US)

(72) Inventors: Robert Bilgor Peliks, San Francisco, CA (US); Darin Charles Gittings, Sunnyvale, CA (US); Hugh Edward Magen, Belmont, CA (US); Uriel Hiram Chee, Santa Cruz, CA (US)

(73) Assignee: Aegea Medical Inc., Redwood City, CA (US)

( * ) Notice: Subject to any disclaimer, the term of this patent is extended or adjusted under 35 U.S.C. 154(b) by 328 days.

(21) Appl. No.: 16/077,542

(22) PCT Filed: Feb. 21, 2017

(86) PCT No.: PCT/US2017/018729
§ 371 (c)(1),
(2) Date: Aug. 13, 2018

(87) PCT Pub. No.: WO2017/143343
PCT Pub. Date: Aug. 24, 2017

(65) Prior Publication Data
US 2019/0038210 A1    Feb. 7, 2019

Related U.S. Application Data

(60) Provisional application No. 62/297,643, filed on Feb. 19, 2016.

(51) Int. Cl.
*A61B 5/00* (2006.01)
*A61B 18/00* (2006.01)
(Continued)

(52) U.S. Cl.
CPC .......... *A61B 5/4325* (2013.01); *A61B 5/4839* (2013.01); *A61B 18/00* (2013.01);
(Continued)

(58) Field of Classification Search
CPC ....... A61B 5/4306–4368; A61B 5/4836–4839; A61B 18/00;
(Continued)

(56) References Cited

U.S. PATENT DOCUMENTS

| 408,899 A | 8/1889 | Small |
| 697,181 A | 4/1902 | Smith |

(Continued)

FOREIGN PATENT DOCUMENTS

| CA | 2851355 A | 4/2013 | ............. A61B 18/18 |
| CN | 201189204 Y | 2/2009 | |

(Continued)

OTHER PUBLICATIONS

Kim et al.; Polyurethanes having shape memory effect; Polymer—Letchworth; 37(26); pp. 5781-5793; Jan. 1996.

(Continued)

*Primary Examiner* — Matthew Kremer
*Assistant Examiner* — Samuel C Kim
(74) *Attorney, Agent, or Firm* — Fish & Richardson P.C.

(57) ABSTRACT

A method and system of providing therapy to a patient's uterus is provided, which can include any number of features. The method can include the steps of inserting a uterine device into the uterus and performing a uterine integrity test to determine that the uterus is intact and not perforated. Systems for performing these methods with monitored flow rate and independent of patient height relative to the pressure source are also disclosed.

16 Claims, 17 Drawing Sheets

(51) Int. Cl.
*A61B 18/04* (2006.01)
*A61B 17/42* (2006.01)
*A61B 90/00* (2016.01)

(52) U.S. Cl.
CPC ...... *A61B 18/04* (2013.01); *A61B 2017/4216* (2013.01); *A61B 2018/0022* (2013.01); *A61B 2018/00559* (2013.01); *A61B 2018/00577* (2013.01); *A61B 2018/046* (2013.01); *A61B 2090/0809* (2016.02)

(58) Field of Classification Search
CPC . A61B 2018/00005–00035; A61B 2018/0016; A61B 2018/00214–00261; A61B 2018/00285; A61B 2018/00559; A61B 2018/00577–00583; A61B 2018/00636–00678; A61B 2018/00744; A61B 18/04; A61B 2018/046; A61B 2018/48; A61B 17/42–46; A61B 2017/4216; A61B 2090/063; A61B 2090/064; A61B 2090/065; A61B 2090/0809; A61B 90/02; A61M 13/00–006; A61M 2205/15
See application file for complete search history.

(56) References Cited

U.S. PATENT DOCUMENTS

| | | |
|---|---|---|
| 1,719,750 A | 7/1929 | Bridge et al. |
| 3,818,913 A | 6/1974 | Wallach |
| 3,871,374 A | 3/1975 | Bolduc et al. |
| 3,880,168 A | 4/1975 | Berman |
| 3,924,628 A | 12/1975 | Droegemueller et al. |
| 3,930,505 A | 1/1976 | Wallach |
| 4,083,077 A | 4/1978 | Knight et al. |
| 4,447,227 A | 5/1984 | Kotsanis |
| 4,672,962 A | 6/1987 | Hershenson |
| 4,682,596 A | 7/1987 | Bales et al. |
| 4,748,979 A | 6/1988 | Hershenson |
| 4,758,228 A * | 7/1988 | Williams ............... A61M 5/142 128/DIG. 12 |
| 4,773,410 A | 9/1988 | Blackmer et al. |
| 4,793,352 A | 12/1988 | Eichenlaub |
| 4,872,920 A | 10/1989 | Flynn et al. |
| 4,898,574 A | 2/1990 | Uchiyama et al. |
| 4,915,113 A | 4/1990 | Holman |
| 4,941,475 A | 7/1990 | Williams et al. |
| 4,950,266 A | 8/1990 | Sinofsky |
| 4,976,711 A | 12/1990 | Parins et al. |
| 4,985,027 A | 1/1991 | Dressel |
| 5,006,119 A | 4/1991 | Acker et al. |
| 5,011,566 A | 4/1991 | Hoffman |
| 5,045,056 A | 9/1991 | Behl |
| 5,078,736 A | 1/1992 | Behl |
| 5,084,043 A | 1/1992 | Hertzmann et al. |
| 5,084,044 A | 1/1992 | Quint |
| 5,102,410 A | 4/1992 | Dressel |
| 5,112,328 A | 5/1992 | Taboada et al. |
| 5,122,138 A | 6/1992 | Manwaring |
| 5,145,935 A | 9/1992 | Hayashi |
| 5,158,536 A | 10/1992 | Sekins et al. |
| 5,162,374 A | 11/1992 | Mulieri et al. |
| 5,190,539 A | 3/1993 | Fletcher et al. |
| 5,217,459 A | 6/1993 | Kamerling |
| 5,217,465 A | 6/1993 | Steppe |
| 5,218,970 A | 6/1993 | Turnbull et al. |
| 5,242,474 A | 9/1993 | Herbst et al. |
| 5,246,436 A | 9/1993 | Rowe |
| 5,263,951 A | 11/1993 | Spears et al. |
| 5,277,201 A | 1/1994 | Stern |
| 5,277,696 A | 1/1994 | Hagen |
| 5,306,274 A | 4/1994 | Long |
| 5,318,014 A | 6/1994 | Carter |
| 5,331,947 A | 7/1994 | Shturman |
| 5,334,190 A | 8/1994 | Seiler |
| 5,344,397 A | 9/1994 | Heaven et al. |
| 5,348,551 A | 9/1994 | Spears et al. |
| 5,352,512 A | 10/1994 | Hoffman |
| 5,411,482 A | 5/1995 | Campbell |
| 5,417,686 A | 5/1995 | Peterson et al. |
| 5,424,620 A | 6/1995 | Cheon et al. |
| 5,433,708 A | 7/1995 | Nichols et al. |
| 5,433,739 A | 7/1995 | Sluijter et al. |
| 5,437,629 A | 8/1995 | Goldrath |
| 5,443,470 A | 8/1995 | Stern et al. |
| 5,445,168 A | 8/1995 | Krebs |
| 5,449,380 A | 9/1995 | Chin |
| 5,451,208 A | 9/1995 | Goldrath |
| 5,462,521 A | 10/1995 | Brucker et al. |
| 5,500,012 A | 3/1996 | Brucker et al. |
| 5,503,638 A | 4/1996 | Cooper et al. |
| 5,505,730 A | 4/1996 | Edwards |
| 5,506,300 A | 4/1996 | Ward et al. |
| 5,524,620 A | 6/1996 | Rosenschein |
| 5,529,076 A | 6/1996 | Schachar |
| 5,540,658 A | 7/1996 | Evans et al. |
| 5,542,928 A | 8/1996 | Evans et al. |
| 5,554,172 A | 9/1996 | Horner et al. |
| 5,562,608 A | 10/1996 | Sekins et al. |
| 5,562,720 A | 10/1996 | Stern et al. |
| 5,584,872 A | 12/1996 | LaFontaine et al. |
| 5,591,157 A | 1/1997 | Hennings et al. |
| 5,616,120 A | 4/1997 | Andrew et al. |
| 5,620,440 A | 4/1997 | Heckele et al. |
| 5,647,871 A | 7/1997 | Levine et al. |
| 5,653,692 A | 8/1997 | Masterson et al. |
| 5,662,671 A | 9/1997 | Barbut et al. |
| 5,665,074 A | 9/1997 | Kelly |
| 5,665,822 A | 9/1997 | Bitler et al. |
| 5,669,907 A | 9/1997 | Platt et al. |
| 5,674,191 A | 10/1997 | Edwards et al. |
| 5,681,282 A | 10/1997 | Eggers et al. |
| 5,683,366 A | 11/1997 | Eggers et al. |
| 5,688,267 A | 11/1997 | Panescu et al. |
| 5,695,507 A | 12/1997 | Auth et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,700,262 A | 12/1997 | Acosta et al. |
| 5,707,352 A | 1/1998 | Sekins et al. |
| 5,730,719 A | 3/1998 | Edwards |
| 5,735,811 A | 4/1998 | Brisken |
| 5,741,247 A | 4/1998 | Rizoiu et al. |
| 5,741,248 A | 4/1998 | Stern et al. |
| 5,743,870 A | 4/1998 | Edwards |
| 5,752,965 A | 5/1998 | Francis et al. |
| 5,754,717 A | 5/1998 | Esch |
| 5,755,753 A | 5/1998 | Knowlton |
| 5,769,880 A | 6/1998 | Truckai et al. |
| 5,782,914 A | 7/1998 | Schankereli |
| 5,785,521 A | 7/1998 | Rizoiu et al. |
| 5,800,379 A | 9/1998 | Edwards |
| 5,800,482 A | 9/1998 | Pomeranz et al. |
| 5,800,493 A | 9/1998 | Stevens et al. |
| 5,810,764 A | 9/1998 | Eggers et al. |
| 5,820,580 A | 10/1998 | Edwards et al. |
| 5,824,703 A | 10/1998 | Clark |
| 5,827,268 A | 10/1998 | Laufer |
| 5,836,896 A | 11/1998 | Rosenschein |
| 5,836,906 A | 11/1998 | Edwards |
| 5,843,019 A | 12/1998 | Eggers et al. |
| 5,871,469 A | 2/1999 | Eggers et al. |
| 5,873,855 A | 2/1999 | Eggers et al. |
| 5,879,329 A | 3/1999 | Ginsburg |
| 5,885,243 A | 3/1999 | Capetan et al. |
| 5,888,198 A | 3/1999 | Eggers et al. |
| 5,891,094 A | 4/1999 | Masterson et al. |
| 5,891,095 A | 4/1999 | Eggers et al. |
| 5,891,134 A | 4/1999 | Goble et al. |
| 5,891,457 A | 4/1999 | Neuwirth |
| 5,902,272 A | 5/1999 | Eggers et al. |
| 5,911,734 A | 6/1999 | Tsugita et al. |

(56) References Cited

U.S. PATENT DOCUMENTS

| | | |
|---|---|---|
| 5,913,856 A | 6/1999 | Chia et al. |
| 5,938,660 A | 8/1999 | Swartz et al. |
| 5,944,686 A | 8/1999 | Patterson et al. |
| 5,944,715 A | 8/1999 | Goble et al. |
| 5,957,919 A | 9/1999 | Laufer |
| 5,964,752 A | 10/1999 | Stone |
| 5,968,037 A | 10/1999 | Rizoiu et al. |
| 5,976,129 A | 11/1999 | Desai |
| 5,980,504 A | 11/1999 | Sharkey et al. |
| 5,986,662 A | 11/1999 | Argiro et al. |
| 5,989,212 A | 11/1999 | Sussman et al. |
| 5,989,249 A | 11/1999 | Kirwan |
| 5,989,445 A | 11/1999 | Wise et al. |
| 5,997,499 A | 12/1999 | Sussman et al. |
| 6,004,509 A | 12/1999 | Dey et al. |
| 6,015,406 A | 1/2000 | Goble et al. |
| 6,024,095 A | 2/2000 | Stanley |
| 6,024,733 A | 2/2000 | Eggers et al. |
| 6,027,501 A | 2/2000 | Goble et al. |
| 6,032,077 A | 2/2000 | Pomeranz |
| 6,045,532 A | 4/2000 | Eggers et al. |
| 6,045,549 A | 4/2000 | Smethers et al. |
| 6,047,700 A | 4/2000 | Eggers et al. |
| 6,053,172 A | 4/2000 | Hovda et al. |
| 6,053,909 A | 4/2000 | Shadduck |
| 6,056,746 A | 5/2000 | Goble et al. |
| 6,057,689 A | 5/2000 | Saadat |
| 6,059,011 A | 5/2000 | Giolo |
| 6,063,079 A | 5/2000 | Hovda et al. |
| 6,063,081 A | 5/2000 | Mulier et al. |
| 6,066,132 A | 5/2000 | Chen et al. |
| 6,066,134 A | 5/2000 | Eggers et al. |
| 6,066,139 A | 5/2000 | Ryan et al. |
| 6,080,128 A | 6/2000 | Sussman et al. |
| 6,080,151 A | 6/2000 | Swartz et al. |
| 6,083,255 A | 7/2000 | Laufer et al. |
| 6,086,585 A | 7/2000 | Hovda et al. |
| 6,095,149 A | 8/2000 | Sharkey et al. |
| 6,099,251 A | 8/2000 | LaFleur |
| 6,102,046 A | 8/2000 | Weinstein et al. |
| 6,102,885 A | 8/2000 | Bass |
| 6,105,581 A | 8/2000 | Eggers et al. |
| 6,106,516 A | 8/2000 | Massengill |
| 6,109,268 A | 8/2000 | Thapliyal et al. |
| 6,113,594 A | 9/2000 | Savage |
| 6,113,597 A | 9/2000 | Eggers et al. |
| 6,113,722 A | 9/2000 | Hoffman et al. |
| 6,117,109 A | 9/2000 | Eggers et al. |
| 6,126,682 A | 10/2000 | Sharkey et al. |
| 6,130,671 A | 10/2000 | Argiro |
| 6,139,571 A | 10/2000 | Fuller et al. |
| 6,149,620 A | 11/2000 | Baker et al. |
| 6,156,036 A | 12/2000 | Sussman et al. |
| 6,159,160 A | 12/2000 | Hsei et al. |
| 6,159,194 A | 12/2000 | Eggers et al. |
| 6,159,207 A | 12/2000 | Yoon |
| 6,159,208 A | 12/2000 | Hovda et al. |
| 6,162,210 A | 12/2000 | Shadduck |
| 6,162,232 A | 12/2000 | Shadduck |
| 6,174,308 B1 | 1/2001 | Goble et al. |
| 6,179,805 B1 | 1/2001 | Sussman et al. |
| 6,179,824 B1 | 1/2001 | Eggers et al. |
| 6,179,836 B1 | 1/2001 | Eggers et al. |
| 6,183,469 B1 | 2/2001 | Thapliyal et al. |
| 6,190,381 B1 | 2/2001 | Olsen et al. |
| 6,194,066 B1 | 2/2001 | Hoffman |
| 6,196,989 B1 | 3/2001 | Padget et al. |
| 6,200,333 B1 | 3/2001 | Laufer |
| 6,203,542 B1 | 3/2001 | Ellsberry et al. |
| 6,210,402 B1 | 4/2001 | Olsen et al. |
| 6,210,404 B1 | 4/2001 | Shadduck |
| 6,210,405 B1 | 4/2001 | Goble et al. |
| 6,219,059 B1 | 4/2001 | Argiro |
| 6,224,592 B1 | 5/2001 | Eggers et al. |
| 6,228,078 B1 | 5/2001 | Eggers et al. |
| 6,228,081 B1 | 5/2001 | Goble |
| 6,228,082 B1 | 5/2001 | Baker et al. |
| 6,231,567 B1 | 5/2001 | Rizoiu et al. |
| 6,235,020 B1 | 5/2001 | Cheng et al. |
| 6,238,391 B1 | 5/2001 | Olsen et al. |
| 6,254,597 B1 | 7/2001 | Rizoiu et al. |
| 6,254,600 B1 | 7/2001 | Willink et al. |
| 6,261,286 B1 | 7/2001 | Goble et al. |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,264,652 B1 | 7/2001 | Eggers et al. |
| 6,277,112 B1 | 8/2001 | Underwood et al. |
| 6,277,114 B1 | 8/2001 | Bullivant et al. |
| 6,283,910 B1 | 9/2001 | Bradshaw et al. |
| 6,283,961 B1 | 9/2001 | Underwood et al. |
| 6,283,989 B1 | 9/2001 | Laufer et al. |
| 6,290,715 B1 | 9/2001 | Sharkey et al. |
| 6,293,942 B1 | 9/2001 | Goble et al. |
| 6,296,636 B1 | 10/2001 | Cheng et al. |
| 6,296,638 B1 | 10/2001 | Davison et al. |
| 6,299,633 B1 | 10/2001 | Laufer |
| 6,300,150 B1 | 10/2001 | Venkatasubramanian |
| 6,306,129 B1 | 10/2001 | Little et al. |
| 6,306,134 B1 | 10/2001 | Goble et al. |
| 6,309,387 B1 | 10/2001 | Eggers et al. |
| 6,312,408 B1 | 11/2001 | Eggers et al. |
| 6,312,474 B1 | 11/2001 | Francis et al. |
| 6,315,755 B1 | 11/2001 | Sussman |
| 6,319,221 B1 | 11/2001 | Savage et al. |
| 6,322,549 B1 | 11/2001 | Eggers et al. |
| 6,327,505 B1 | 12/2001 | Medhkour et al. |
| 6,328,735 B1 | 12/2001 | Curley et al. |
| 6,331,171 B1 | 12/2001 | Cohen |
| 6,355,032 B1 | 3/2002 | Hovda et al. |
| 6,361,531 B1 | 3/2002 | Hissong |
| 6,363,937 B1 | 4/2002 | Hovda et al. |
| 6,364,877 B1 | 4/2002 | Goble et al. |
| 6,375,635 B1 | 4/2002 | Moutafis et al. |
| 6,379,350 B1 | 4/2002 | Sharkey et al. |
| 6,379,351 B1 | 4/2002 | Thapliyal et al. |
| 6,387,088 B1 | 5/2002 | Shadduck et al. |
| 6,388,043 B1 | 5/2002 | Langer et al. |
| 6,391,025 B1 | 5/2002 | Weinstein et al. |
| 6,394,949 B1 | 5/2002 | Crowley et al. |
| 6,394,996 B1 | 5/2002 | Lawrence et al. |
| 6,398,759 B1 | 6/2002 | Sussman et al. |
| 6,398,775 B1 | 6/2002 | Perkins et al. |
| 6,409,699 B1 | 6/2002 | Ash |
| 6,409,723 B1 | 6/2002 | Edwards |
| 6,425,877 B1 | 6/2002 | Edwards |
| 6,416,507 B1 | 7/2002 | Eggers et al. |
| 6,416,508 B1 | 7/2002 | Eggers et al. |
| 6,416,509 B1 | 7/2002 | Goble et al. |
| 6,425,867 B1 | 7/2002 | Vaezy et al. |
| 6,432,103 B1 | 8/2002 | Ellsberry et al. |
| 6,440,089 B1 | 8/2002 | Shine |
| 6,443,947 B1 * | 9/2002 | Marko .................. A61B 18/08 606/28 |
| 6,451,012 B2 | 9/2002 | Dobak, III |
| 6,458,231 B1 | 10/2002 | Wapner et al. |
| 6,461,350 B1 | 10/2002 | Underwood et al. |
| 6,461,354 B1 | 10/2002 | Olsen et al. |
| 6,464,694 B1 | 10/2002 | Massengill |
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,468,313 B1 | 10/2002 | Claeson et al. |
| 6,475,215 B1 | 11/2002 | Tanrisever |
| 6,482,201 B1 | 11/2002 | Olsen et al. |
| 6,488,673 B1 | 12/2002 | Laufer et al. |
| 6,493,589 B1 | 12/2002 | Medhkour et al. |
| 6,500,173 B2 | 12/2002 | Underwood et al. |
| 6,508,816 B2 | 1/2003 | Shadduck |
| 6,510,854 B2 | 1/2003 | Goble |
| 6,517,533 B1 | 2/2003 | Swaminathan |
| 6,522,930 B1 | 2/2003 | Schaer et al. |
| 6,527,761 B1 | 3/2003 | Soltesz et al. |
| 6,527,766 B1 | 3/2003 | Bair |

(56) References Cited

U.S. PATENT DOCUMENTS

| | | |
|---|---|---|
| 6,540,741 B1 | 4/2003 | Underwood et al. |
| 6,544,211 B1 | 4/2003 | Andrew et al. |
| 6,544,261 B2 | 4/2003 | Ellsberry et al. |
| 6,547,784 B1 | 4/2003 | Thompson et al. |
| 6,551,271 B2 | 4/2003 | Nguyen |
| 6,551,274 B2 | 4/2003 | Heiner |
| 6,554,780 B1 | 4/2003 | Sampson et al. |
| 6,557,559 B1 | 5/2003 | Eggers et al. |
| 6,558,379 B1 | 5/2003 | Batchelor et al. |
| 6,565,561 B1 | 5/2003 | Goble et al. |
| 6,569,146 B1 | 5/2003 | Werner et al. |
| 6,575,929 B2 | 6/2003 | Sussman et al. |
| 6,575,933 B1 | 6/2003 | Wittenberger et al. |
| 6,575,968 B1 | 6/2003 | Eggers et al. |
| 6,579,270 B2 | 6/2003 | Sussman et al. |
| 6,582,423 B1 | 6/2003 | Thapliyal et al. |
| 6,585,639 B1 | 7/2003 | Kotmel et al. |
| 6,588,613 B1 | 7/2003 | Pechenik et al. |
| 6,589,201 B1 | 7/2003 | Sussman et al. |
| 6,589,237 B2 | 7/2003 | Woloszko et al. |
| 6,592,594 B2 | 7/2003 | Rimbaugh et al. |
| 6,595,990 B1 | 7/2003 | Weinstein et al. |
| 6,599,311 B1 | 7/2003 | Biggs et al. |
| 6,602,248 B1 | 8/2003 | Sharps et al. |
| 6,610,043 B1 | 8/2003 | Ingenito |
| 6,620,155 B2 | 9/2003 | Underwood et al. |
| 6,623,444 B2 | 9/2003 | Babaev |
| 6,626,855 B1 | 9/2003 | Weng et al. |
| 6,629,974 B2 | 10/2003 | Penny et al. |
| 6,632,193 B1 | 10/2003 | Davison et al. |
| 6,632,220 B1 | 10/2003 | Eggers et al. |
| 6,634,363 B1 | 10/2003 | Danek et al. |
| 6,653,525 B2 | 11/2003 | Ingenito et al. |
| 6,669,685 B1 | 12/2003 | Rizoiu et al. |
| 6,669,694 B2 | 12/2003 | Shadduck |
| 6,676,628 B2 | 1/2004 | Sussman et al. |
| 6,676,629 B2 | 1/2004 | Andrew et al. |
| 6,679,264 B1 | 1/2004 | Deem et al. |
| 6,679,879 B2 | 1/2004 | Shadduck |
| 6,692,490 B1 | 2/2004 | Edwards |
| 6,692,494 B1 | 2/2004 | Cooper et al. |
| 6,695,839 B2 | 2/2004 | Sharkey et al. |
| 6,699,212 B1 | 3/2004 | Kadziauskas et al. |
| 6,699,244 B2 | 3/2004 | Carranza et al. |
| 6,708,056 B2 | 3/2004 | Duchon et al. |
| 6,712,811 B2 | 3/2004 | Underwood et al. |
| 6,712,812 B2 | 3/2004 | Roschak et al. |
| 6,719,754 B2 | 4/2004 | Underwood et al. |
| 6,726,684 B1 | 4/2004 | Woloszko et al. |
| 6,726,708 B2 | 4/2004 | Lasheras |
| 6,743,184 B2 | 6/2004 | Sampson et al. |
| 6,743,197 B1 | 6/2004 | Edwards |
| 6,746,447 B2 | 6/2004 | Davison et al. |
| 6,749,604 B1 | 6/2004 | Eggers et al. |
| 6,755,794 B2 | 6/2004 | Soukup |
| 6,758,846 B2 | 7/2004 | Goble et al. |
| 6,763,836 B2 | 7/2004 | Tasto et al. |
| 6,766,202 B2 | 7/2004 | Underwood et al. |
| 6,770,070 B1 | 8/2004 | Balbierz |
| 6,770,071 B2 | 8/2004 | Woloszko et al. |
| 6,772,012 B2 | 8/2004 | Ricart et al. |
| 6,773,431 B2 | 8/2004 | Eggers et al. |
| 6,776,765 B2 | 8/2004 | Soukup et al. |
| 6,780,180 B1 | 8/2004 | Goble et al. |
| 6,805,130 B2 | 10/2004 | Tasto et al. |
| 6,813,520 B2 | 11/2004 | Truckai et al. |
| 6,832,996 B2 | 12/2004 | Woloszko et al. |
| 6,837,884 B2 | 1/2005 | Woloszko |
| 6,837,887 B2 | 1/2005 | Woloszko et al. |
| 6,837,888 B2 | 1/2005 | Ciarrocca et al. |
| 6,852,108 B2 | 2/2005 | Barry et al. |
| 6,860,847 B2 | 3/2005 | Alferness et al. |
| 6,872,183 B2 | 3/2005 | Sampson et al. |
| 6,875,194 B2 | 4/2005 | MacKool |
| 6,896,672 B1 | 5/2005 | Eggers et al. |
| 6,896,674 B1 | 5/2005 | Woloszko et al. |
| 6,896,675 B2 | 5/2005 | Leung et al. |
| 6,896,690 B1 | 5/2005 | Lambrecht et al. |
| 6,901,927 B2 | 6/2005 | Deem et al. |
| 6,904,909 B2 | 6/2005 | Andreas et al. |
| 6,907,881 B2 | 6/2005 | Suki et al. |
| 6,911,028 B2 | 6/2005 | Shadduck |
| 6,915,806 B2 | 7/2005 | Pacek et al. |
| 6,918,903 B2 | 7/2005 | Bass |
| 6,921,385 B2 | 7/2005 | Clements et al. |
| 6,929,640 B1 | 8/2005 | Underwood et al. |
| 6,929,642 B2 | 8/2005 | Xiao et al. |
| 6,949,096 B2 | 9/2005 | Davison et al. |
| 6,955,675 B2 | 10/2005 | Jain |
| 6,960,204 B2 | 11/2005 | Eggers et al. |
| 6,962,584 B1 | 11/2005 | Stone et al. |
| 6,972,014 B2 | 12/2005 | Eum et al. |
| 6,978,174 B2 | 12/2005 | Gelfand et al. |
| 6,986,769 B2 | 1/2006 | Nelson et al. |
| 6,991,028 B2 | 1/2006 | Comeaux et al. |
| 6,991,631 B2 | 1/2006 | Woloszko et al. |
| 7,004,940 B2 | 2/2006 | Ryan et al. |
| 7,004,941 B2 | 2/2006 | Tvinnereim et al. |
| 7,022,088 B2 | 4/2006 | Keast et al. |
| 7,022,105 B1 | 4/2006 | Edwards |
| 7,031,504 B1 | 4/2006 | Argiro et al. |
| 7,063,670 B2 | 6/2006 | Sampson et al. |
| 7,070,596 B1 | 7/2006 | Woloszko et al. |
| 7,083,612 B2 | 8/2006 | Littrup et al. |
| 7,094,215 B2 | 8/2006 | Davison et al. |
| 7,094,249 B1 | 8/2006 | Broome et al. |
| 7,101,367 B2 | 9/2006 | Xiao et al. |
| 7,104,986 B2 | 9/2006 | Hovda et al. |
| 7,105,007 B2 | 9/2006 | Hibler |
| RE39,358 E | 10/2006 | Goble |
| 7,128,748 B2 | 10/2006 | Mooradian et al. |
| 7,131,969 B1 | 11/2006 | Hovda et al. |
| 7,136,064 B2 | 11/2006 | Zuiderveld |
| 7,144,402 B2 | 12/2006 | Kuester |
| 7,144,588 B2 | 12/2006 | Oray et al. |
| 7,162,303 B2 | 1/2007 | Levin et al. |
| 7,169,143 B2 | 1/2007 | Eggers et al. |
| 7,179,255 B2 | 2/2007 | Lettice et al. |
| 7,186,234 B2 | 3/2007 | Dahla et al. |
| 7,192,400 B2 | 3/2007 | Campbell et al. |
| 7,192,428 B2 | 3/2007 | Eggers et al. |
| 7,201,750 B1 | 4/2007 | Eggers et al. |
| 7,217,268 B2 | 5/2007 | Eggers et al. |
| 7,233,820 B2 | 6/2007 | Gilboa |
| 7,235,070 B2 | 6/2007 | Vanney |
| 7,241,293 B2 | 7/2007 | Davison |
| 7,270,658 B2 | 9/2007 | Woloszko et al. |
| 7,270,659 B2 | 9/2007 | Ricart et al. |
| 7,270,661 B2 | 9/2007 | Dahla et al. |
| 7,276,063 B2 | 10/2007 | Davison et al. |
| 7,297,143 B2 | 11/2007 | Woloszko et al. |
| 7,297,145 B2 | 11/2007 | Woloszko et al. |
| 7,311,708 B2 | 12/2007 | McClurken |
| 7,320,325 B2 | 1/2008 | Duchon et al. |
| 7,326,235 B2 | 2/2008 | Edwards |
| 7,331,957 B2 | 2/2008 | Woloszko et al. |
| 7,335,195 B2 | 2/2008 | Mehier |
| 7,347,859 B2 | 3/2008 | Garabedian et al. |
| 7,512,445 B2 | 3/2009 | Truckai et al. |
| 7,524,315 B2 | 4/2009 | Blott et al. |
| 7,585,295 B2 | 9/2009 | Ben-Nun |
| 7,617,005 B2 | 11/2009 | Demarais et al. |
| 7,620,451 B2 | 11/2009 | Demarais et al. |
| 7,653,438 B2 | 1/2010 | Deem et al. |
| 7,717,909 B2 | 5/2010 | Strul et al. |
| 7,756,583 B2 | 7/2010 | Demarais et al. |
| 7,815,616 B2 | 10/2010 | Boehringer et al. |
| 7,815,646 B2 | 10/2010 | Hart |
| 7,846,160 B2 | 12/2010 | Payne et al. |
| 7,853,333 B2 | 12/2010 | Demarais |
| 7,873,417 B2 | 1/2011 | Demarais et al. |
| 7,937,143 B2 | 5/2011 | Demarais et al. |
| 7,993,323 B2 | 8/2011 | Barry et al. |
| 8,025,656 B2 | 9/2011 | Gruber et al. |

(56) References Cited

U.S. PATENT DOCUMENTS

| | | |
|---|---|---|
| 8,131,371 B2 | 3/2012 | Demarais et al. |
| 8,145,316 B2 | 3/2012 | Deem et al. |
| 8,145,317 B2 | 3/2012 | Demarais et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,192,424 B2 | 6/2012 | Woloszko |
| 8,197,470 B2 | 6/2012 | Sharkey et al. |
| 8,216,217 B2 | 7/2012 | Sharkey et al. |
| 8,221,401 B2 | 7/2012 | Sharkey et al. |
| 8,221,403 B2 | 7/2012 | Sharkey et al. |
| 8,226,645 B2 | 7/2012 | Harrington et al. |
| 8,313,485 B2 | 11/2012 | Shadduck |
| 8,343,078 B2 | 1/2013 | Toth |
| 8,394,037 B2 * | 3/2013 | Toth ............... A61B 5/4325 600/591 |
| 8,486,060 B2 | 7/2013 | Kotmel et al. |
| 8,500,732 B2 | 8/2013 | Truckai et al. |
| 8,506,563 B2 | 8/2013 | Truckai et al. |
| 8,529,562 B2 | 9/2013 | Vissy et al. |
| 8,540,708 B2 | 9/2013 | Truckai et al. |
| 8,551,082 B2 | 10/2013 | Strul et al. |
| 8,574,226 B2 | 11/2013 | Shadduck |
| 8,579,888 B2 | 11/2013 | Hoey et al. |
| 8,579,892 B2 | 11/2013 | Hoey et al. |
| 8,585,645 B2 | 11/2013 | Barry et al. |
| 8,585,692 B2 | 11/2013 | Shadduck et al. |
| 8,597,289 B2 | 12/2013 | Layton, Jr. et al. |
| 8,647,349 B2 | 2/2014 | Gruber et al. |
| 8,690,873 B2 | 4/2014 | Truckai et al. |
| 8,715,278 B2 | 5/2014 | Toth et al. |
| 8,721,632 B2 | 5/2014 | Hoey et al. |
| 8,758,341 B2 | 6/2014 | Shadduck |
| 8,801,702 B2 | 8/2014 | Hoey et al. |
| 8,814,796 B2 | 8/2014 | Martin et al. |
| 8,840,625 B2 | 9/2014 | Adams et al. |
| 8,900,223 B2 | 12/2014 | Shadduck |
| 8,926,629 B2 | 1/2015 | Truckai |
| 8,936,592 B2 | 1/2015 | Beck et al. |
| 8,939,971 B2 | 1/2015 | Truckai et al. |
| 8,956,348 B2 | 2/2015 | Bek |
| 8,998,898 B2 | 4/2015 | Truckai et al. |
| 8,998,901 B2 | 4/2015 | Truckai et al. |
| 9,050,102 B2 | 6/2015 | TruckaI |
| 9,050,103 B2 | 6/2015 | Truckai |
| 9,095,348 B2 | 8/2015 | Truckai et al. |
| 9,113,944 B2 | 8/2015 | Shadduck |
| 9,144,421 B1 | 9/2015 | Lau et al. |
| 9,186,208 B2 | 11/2015 | Truckai et al. |
| 9,204,889 B2 | 12/2015 | Shadduck |
| 9,242,122 B2 | 1/2016 | Tsoref et al. |
| 9,247,989 B2 | 2/2016 | Truckai |
| 9,259,262 B2 | 2/2016 | Hundertmark et al. |
| 9,265,921 B2 * | 2/2016 | Korman ............... A61B 90/02 |
| 9,277,952 B2 | 3/2016 | Burnett et al. |
| 9,283,022 B2 | 3/2016 | Burnett et al. |
| 9,289,257 B2 | 3/2016 | Toth et al. |
| 9,333,111 B2 | 5/2016 | Kochem et al. |
| 9,339,330 B2 | 5/2016 | Truckai |
| 9,408,657 B2 | 8/2016 | Burnett et al. |
| 9,421,059 B2 | 8/2016 | Truckai et al. |
| 9,427,556 B2 | 8/2016 | Burnett |
| 9,433,457 B2 | 9/2016 | Shadduck |
| 9,433,467 B2 | 9/2016 | Beck et al. |
| 9,486,267 B2 | 11/2016 | Burnett et al. |
| 9,498,274 B2 | 11/2016 | Burnett et al. |
| 9,554,853 B2 | 1/2017 | Strul et al. |
| 9,585,712 B2 | 3/2017 | Truckai |
| 9,615,875 B2 | 4/2017 | Shadduck |
| 9,636,171 B2 | 5/2017 | Toth et al. |
| 9,662,060 B2 | 5/2017 | Peliks et al. |
| 9,662,163 B2 | 5/2017 | Toth et al. |
| 9,743,974 B2 | 8/2017 | Gurskis et al. |
| 9,743,978 B2 | 8/2017 | Skalyni |
| 9,775,542 B2 | 10/2017 | Toth |
| 9,788,890 B2 | 10/2017 | Toth et al. |
| 9,814,520 B2 | 11/2017 | Truckai |
| 9,848,933 B2 | 12/2017 | Burnett et al. |
| 9,883,907 B2 | 2/2018 | Toth et al. |
| 9,895,192 B2 | 2/2018 | Model |
| 9,907,599 B2 | 3/2018 | Hoey et al. |
| 9,913,681 B2 | 3/2018 | Bueaudet |
| 9,943,353 B2 | 4/2018 | Hoey et al. |
| 9,993,290 B2 | 6/2018 | Chee et al. |
| 10,004,551 B2 | 6/2018 | Burnett et al. |
| 10,004,553 B2 | 7/2018 | Churchill et al. |
| 10,052,150 B2 | 8/2018 | Truckai et al. |
| 10,105,176 B2 | 10/2018 | Toth et al. |
| 10,179,019 B2 | 1/2019 | Chee et al. |
| 10,213,151 B2 | 2/2019 | Filloux et al. |
| 10,213,335 B2 | 2/2019 | Burnett et al. |
| 10,238,446 B2 | 3/2019 | Gurskis et al. |
| 10,299,856 B2 | 5/2019 | Chee et al. |
| 10,456,194 B2 | 10/2019 | Truckai |
| 10,499,981 B2 | 12/2019 | Model |
| 10,524,847 B2 | 1/2020 | Shadduck |
| 10,548,653 B2 | 2/2020 | Hoey et al. |
| 10,575,898 B2 | 3/2020 | Chee et al. |
| 10,588,689 B2 | 3/2020 | Truckai |
| 10,617,461 B2 | 4/2020 | Toth et al. |
| 10,624,694 B2 | 4/2020 | Kochem et al. |
| 10,722,298 B2 | 7/2020 | Skalnyi |
| 10,758,300 B2 | 9/2020 | Truckai et al. |
| 10,779,877 B2 | 9/2020 | Churchill et al. |
| 2002/0007180 A1 | 1/2002 | Wittenberger et al. |
| 2002/0013601 A1 | 1/2002 | Nobles et al. |
| 2002/0019627 A1 | 2/2002 | Maguire et al. |
| 2002/0077516 A1 | 6/2002 | Flanigan |
| 2002/0078956 A1 | 6/2002 | Sharpe et al. |
| 2002/0111386 A1 | 8/2002 | Sekins et al. |
| 2002/0128638 A1 | 9/2002 | Chauvet et al. |
| 2002/0133147 A1 | 9/2002 | Marchitto et al. |
| 2002/0151917 A1 | 10/2002 | Barry |
| 2002/0161326 A1 | 10/2002 | Sussman et al. |
| 2002/0173815 A1 | 11/2002 | Hogendijk et al. |
| 2002/0177846 A1 | 11/2002 | Mulier et al. |
| 2003/0028189 A1 | 2/2003 | Woloszko et al. |
| 2003/0097126 A1 | 5/2003 | Woloszko et al. |
| 2003/0099279 A1 | 5/2003 | Venkatasubramanian et al. |
| 2003/0130738 A1 | 7/2003 | Hovda et al. |
| 2003/0144654 A1 | 7/2003 | Hilal |
| 2003/0158545 A1 | 8/2003 | Hovda et al. |
| 2003/0163178 A1 | 8/2003 | Davison et al. |
| 2003/0181922 A1 | 9/2003 | Alferness |
| 2003/0212394 A1 | 11/2003 | Pearson et al. |
| 2003/0217962 A1 | 11/2003 | Childers et al. |
| 2003/0220604 A1 | 11/2003 | Al-Anazi |
| 2003/0225364 A1 | 12/2003 | Kraft et al. |
| 2004/0002698 A1 | 1/2004 | Hua Xiao et al. |
| 2004/0024399 A1 | 2/2004 | Sharps et al. |
| 2004/0047855 A1 | 3/2004 | Ingenito |
| 2004/0049180 A1 | 3/2004 | Sharps et al. |
| 2004/0055606 A1 | 3/2004 | Hendricksen et al. |
| 2004/0068306 A1 | 4/2004 | Shadduck |
| 2004/0116922 A1 | 6/2004 | Hovda et al. |
| 2004/0199226 A1 | 10/2004 | Shadduck |
| 2004/0230190 A1 | 11/2004 | Dahla et al. |
| 2005/0010205 A1 | 1/2005 | Hovda et al. |
| 2005/0119650 A1 | 6/2005 | Sanders et al. |
| 2005/0143728 A1 | 6/2005 | Sampson et al. |
| 2005/0165324 A1 * | 7/2005 | Receveur ............... A61B 34/20 600/549 |
| 2005/0166925 A1 | 8/2005 | Wilson et al. |
| 2005/0171574 A1 | 8/2005 | Rubinsky et al. |
| 2005/0171582 A1 | 8/2005 | Matlock |
| 2005/0177147 A1 | 8/2005 | Vancelette et al. |
| 2005/0182449 A1 * | 8/2005 | Auge II ............... A61B 18/14 607/3 |
| 2005/0215991 A1 | 9/2005 | Altman et al. |
| 2005/0222485 A1 | 10/2005 | Shaw et al. |
| 2005/0228423 A1 | 10/2005 | Khashayar et al. |
| 2005/0228424 A1 | 10/2005 | Khashayar et al. |
| 2005/0240171 A1 | 10/2005 | Forrest |
| 2005/0240239 A1 | 10/2005 | Boveja et al. |

(56) References Cited

U.S. PATENT DOCUMENTS

| | | |
|---|---|---|
| 2005/0267467 A1 | 12/2005 | Paul et al. |
| 2005/0283143 A1 | 12/2005 | Rizoiu |
| 2006/0004400 A1 | 1/2006 | McGurk et al. |
| 2006/0047291 A1 | 3/2006 | Barry |
| 2006/0058831 A1 | 3/2006 | Atad |
| 2006/0085054 A1 | 4/2006 | Zikorus et al. |
| 2006/0100619 A1 | 5/2006 | McClurken et al. |
| 2006/0130830 A1 | 6/2006 | Barry |
| 2006/0135955 A1 | 6/2006 | Shadduck |
| 2006/0142783 A1 | 6/2006 | Lewis et al. |
| 2006/0161147 A1 | 7/2006 | Privitera et al. |
| 2006/0161233 A1 | 7/2006 | Barry et al. |
| 2006/0200076 A1 | 9/2006 | Gonzalez et al. |
| 2006/0206150 A1 | 9/2006 | Demarais et al. |
| 2006/0211914 A1* | 9/2006 | Hassler, Jr. ............ A61F 5/0003 600/37 |
| 2006/0224154 A1 | 10/2006 | Shadduck et al. |
| 2006/0265053 A1 | 11/2006 | Hunt |
| 2006/0271111 A1 | 11/2006 | Demarais et al. |
| 2007/0021713 A1 | 1/2007 | Kumar et al. |
| 2007/0032785 A1 | 2/2007 | Diederich et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0225744 A1 | 9/2007 | Nobles et al. |
| 2007/0239197 A1 | 10/2007 | Dubey et al. |
| 2007/0288051 A1 | 12/2007 | Beyer et al. |
| 2008/0033493 A1 | 2/2008 | Deckman et al. |
| 2008/0077201 A1 | 3/2008 | Levinson et al. |
| 2008/0125747 A1 | 5/2008 | Prokop |
| 2008/0132826 A1 | 6/2008 | Shadduck et al. |
| 2008/0135053 A1 | 6/2008 | Gruber et al. |
| 2008/0161788 A1 | 7/2008 | Dando et al. |
| 2008/0167664 A1 | 7/2008 | Payne et al. |
| 2008/0249467 A1 | 10/2008 | Burnett et al. |
| 2009/0024108 A1 | 1/2009 | Lee-Sepsick et al. |
| 2009/0030412 A1 | 1/2009 | Willis et al. |
| 2009/0076409 A1 | 3/2009 | Wu et al. |
| 2009/0125010 A1 | 5/2009 | Sharkey et al. |
| 2009/0216220 A1 | 8/2009 | Hoey et al. |
| 2009/0306640 A1 | 12/2009 | Glaze et al. |
| 2010/0078046 A1 | 4/2010 | Labib et al. |
| 2010/0082021 A1 | 4/2010 | Gutierrez et al. |
| 2010/0094268 A1 | 4/2010 | Bouthillier et al. |
| 2010/0094270 A1 | 4/2010 | Sharma |
| 2010/0100091 A1 | 4/2010 | Truckai |
| 2010/0100094 A1 | 4/2010 | Truckai |
| 2010/0106152 A1 | 4/2010 | Truckai et al. |
| 2010/0114083 A1 | 5/2010 | Sharma |
| 2010/0114089 A1 | 5/2010 | Truckai et al. |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0179528 A1 | 7/2010 | Shadduck et al. |
| 2010/0204688 A1 | 8/2010 | Hoey et al. |
| 2010/0228222 A1 | 9/2010 | Williams et al. |
| 2010/0249773 A1 | 9/2010 | Clark et al. |
| 2010/0262133 A1 | 10/2010 | Hoey et al. |
| 2011/0009829 A1 | 1/2011 | Kosinski et al. |
| 2011/0054508 A1 | 3/2011 | Zhou et al. |
| 2011/0077628 A1 | 3/2011 | Hoey et al. |
| 2011/0112400 A1 | 5/2011 | Emery et al. |
| 2011/0112432 A1 | 5/2011 | Toth |
| 2011/0112433 A1 | 5/2011 | Toth |
| 2011/0112523 A1 | 5/2011 | Toth et al. |
| 2011/0118718 A1 | 5/2011 | Toth et al. |
| 2011/0118719 A1 | 5/2011 | Vissy et al. |
| 2011/0160648 A1 | 6/2011 | Hoey |
| 2011/0166499 A1 | 7/2011 | Demarais et al. |
| 2011/0178570 A1 | 7/2011 | Demarais |
| 2011/0200171 A1 | 8/2011 | Beetel et al. |
| 2011/0208096 A1 | 8/2011 | Demarais et al. |
| 2011/0208178 A1 | 8/2011 | Truckai |
| 2011/0257564 A1 | 10/2011 | Demarais et al. |
| 2011/0264011 A1 | 10/2011 | Wu et al. |
| 2011/0264075 A1 | 10/2011 | Leung et al. |
| 2011/0264090 A1 | 10/2011 | Shadduck et al. |
| 2011/0275885 A1 | 11/2011 | Bouche |
| 2012/0035471 A1 | 2/2012 | Lee-Sepsick et al. |
| 2012/0065632 A1 | 3/2012 | Shadduck |
| 2012/0101413 A1 | 4/2012 | Beetel et al. |
| 2012/0101538 A1 | 4/2012 | Ballakur et al. |
| 2012/0116382 A1 | 5/2012 | Ku et al. |
| 2012/0116383 A1 | 5/2012 | Mauch et al. |
| 2012/0116486 A1 | 5/2012 | Naga et al. |
| 2012/0130359 A1 | 5/2012 | Turovskiy |
| 2012/0130360 A1 | 5/2012 | Buckley et al. |
| 2012/0130458 A1 | 5/2012 | Ryba et al. |
| 2012/0136343 A1 | 5/2012 | Burnett |
| 2012/0136344 A1 | 5/2012 | Buckley et al. |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143293 A1 | 6/2012 | Mauch et al. |
| 2012/0150267 A1 | 6/2012 | Buckley et al. |
| 2012/0158104 A1 | 6/2012 | Huynh et al. |
| 2012/0172888 A1* | 7/2012 | Shugrue ................ A61B 17/42 606/119 |
| 2012/0197198 A1 | 8/2012 | Demarais et al. |
| 2012/0197245 A1 | 8/2012 | Burnett et al. |
| 2012/0209281 A1 | 8/2012 | Truckai |
| 2012/0232545 A1 | 9/2012 | Truckai et al. |
| 2012/0245583 A1 | 9/2012 | Truckai et al. |
| 2012/0259271 A1 | 10/2012 | Shadduck et al. |
| 2012/0283717 A1 | 11/2012 | Sharkey et al. |
| 2012/0316460 A1 | 12/2012 | Stout |
| 2013/0006231 A1 | 1/2013 | Sharma et al. |
| 2013/0090572 A1* | 4/2013 | Peliks .................. A61B 5/4325 600/591 |
| 2013/0116683 A1 | 5/2013 | Shadduck et al. |
| 2013/0237978 A1 | 9/2013 | Shadduck et al. |
| 2013/0261539 A1* | 10/2013 | King ..................... A61M 31/00 604/65 |
| 2013/0296837 A1 | 11/2013 | Burnett et al. |
| 2014/0031805 A1 | 1/2014 | Shadduck |
| 2014/0088575 A1* | 3/2014 | Loeb ....................... A61B 18/24 606/7 |
| 2014/0088581 A1 | 3/2014 | Kelly et al. |
| 2014/0200570 A1 | 7/2014 | Hoey et al. |
| 2014/0236129 A1* | 8/2014 | Radl ..................... A61M 1/0084 604/540 |
| 2015/0025515 A1 | 1/2015 | Hoey et al. |
| 2015/0119795 A1 | 4/2015 | Germain et al. |
| 2015/0334079 A1* | 11/2015 | Laidlaw ................ H04W 4/60 340/539.11 |
| 2015/0335373 A1 | 11/2015 | Chee et al. |
| 2017/0258511 A1 | 9/2017 | Peliks et al. |
| 2017/0354452 A1 | 12/2017 | Gurskis et al. |
| 2018/0168713 A1 | 6/2018 | Hoey et al. |
| 2018/0193079 A1 | 7/2018 | Hoey et al. |
| 2018/0199982 A1 | 7/2018 | Hoey et al. |
| 2018/0289416 A1 | 10/2018 | Chee et al. |
| 2019/0117289 A1 | 4/2019 | Sharkey et al. |
| 2019/0117290 A1 | 4/2019 | Sharkey et al. |
| 2019/0216523 A1 | 7/2019 | Gurskis et al. |
| 2019/0223934 A1 | 7/2019 | Shadduck |

FOREIGN PATENT DOCUMENTS

| | | | |
|---|---|---|---|
| CN | 201379631 Y | 1/2010 | |
| CN | 101951846 A | 1/2011 | ............ A61B 17/42 |
| CN | 102271602 A | 12/2011 | |
| CN | 102355864 A | 2/2012 | ............ A61B 18/04 |
| CN | 102525548 A | 7/2012 | .............. A61B 8/00 |
| CN | 103717126 A | 4/2014 | ............ A61M 31/00 |
| CN | 104135960 | 5/2014 | ............ A61B 18/18 |
| CN | 104042342 A | 9/2014 | ............ A61B 18/18 |
| JP | H06-285074 A | 10/1994 | |
| JP | 2000502585 A | 3/2000 | |
| JP | 20003513742 A | 4/2003 | |
| JP | 2010516351 A | 5/2010 | |
| WO | WO99/53853 A1 | 10/1999 | |

(56) References Cited

FOREIGN PATENT DOCUMENTS

| WO | WO00/011927 A2 | 3/2000 | |
|---|---|---|---|
| WO | WO00/29055 A1 | 5/2000 | |
| WO | WO01/85012 A2 | 11/2001 | |
| WO | WO02/069821 A1 | 9/2002 | |
| WO | WO 03/070302 A1 | 8/2003 | |
| WO | WO2005/025635 A2 | 3/2005 | |
| WO | WO2005/102175 A2 | 11/2005 | |
| WO | WO2006/003665 A2 | 1/2006 | |
| WO | WO 2006/055695 A1 | 5/2006 | |
| WO | WO2006/108974 A1 | 10/2006 | |
| WO | WO2009/009398 A1 | 1/2009 | |
| WO | WO2010/045055 A2 | 4/2010 | |
| WO | WO2010/048007 A1 | 4/2010 | |
| WO | WO2011/025658 A1 | 3/2011 | |
| WO | WO2011/053599 A1 | 5/2011 | |
| WO | WO2011/060189 A1 | 5/2011 | |
| WO | WO2011/060191 A1 | 5/2011 | |
| WO | WO2012/106260 A2 | 8/2012 | |
| WO | WO 2012/106474 | 8/2012 | ............. A61B 1/303 |

OTHER PUBLICATIONS

Poco; Industry news: Poco introduces improved CXT-CXT-xtra; 2 pages; retrieved from the internet (https://web.archive.org/web/20061215223908/http://www.poco.com/us/) on Feb. 2020.

Stanford; Capacitor micro machined ultrasonic transducer (cMUT); 10 pages; retrieved from the internet (https://web.archive.org/web/20040205083311/http://acoustics.stanford.edu/group/cmut1.pdf) on Feb. 20, 2020.

Baker et al.; Threshold intrauterine perfusion pressures for intraperitoneal spill during hydrotubation and correlation with tubal adhesive diseases; Fertility and Sterility; 64(6); pp. 1066-1069; Dec. 31, 1995.

Blacker; Vaporization of the uterus; J. Obstet. & Gyn.; vol. 1; Issue 5; pp. 488-511; May 1902.

Fishman et. al.; A randomized trial comparing lung-volume-reduction surgery with medical therapy for severe emphysema; N Engl J Med; 348(210. pp. 2059-2073; May 22, 2003.

Homasson et. al.; Bronchoscopic cryotherapy for airway strictures caused by tumors; Chest; 90(2); pp. 159-164; Aug. 1, 1986.

Marasso et al.; Radiofrequency resection of bronchial tumours in combination with cryotherapy: evaluation of a new technique; Thorax; 53(2); pp. 106-109; Feb. 1998.

Marasso et. al.; Cryosurgery in bronchoscopic treatment of tracheobronchial stenosis; Cheat; 103(2); pp. 472-474; Feb. 1993.

Morice et. al; Endobronchial argon plasma coagulation for treatment of hemoptysis and neoplastic airway obstruction; Chest; 119(3); pp. 781-787; Mar. 1, 2001.

Neuwirth et al.; The endometrial ablator: a new instrument; Obst. & Gyn.; vol. 83; No. 5; part 1; pp. 792-796; May 1994.

Prior et al.; Treatment of mennorrhagia by radiofrequency heating; Int. J. Hyperthermia; vol. 7; No. 2; pp. 213-220; Mar.-Apr. 1991.

Tschirren et. al.; Intrathoracic airway trees: segmentation and airway morphology analysis from low-dose CT scans; IEEE Transactions on Medical Imaging; 24(12); pp. 1529-1539; Dec. 2005.

Unger et. al.; Monolithic Microfabricated Valves and Pumps by Multilayer Soft Lithography; Science, 288(5463); pp. 113-116; Apr. 7, 2000.

Van De Velde; Vapo-cauterization of the uterus; Amer. J. Med. Sci.; vol. CXVIII (118); Nov. 1899.

Chee et al.; U.S. Appl. No. 16/422,835 entitled "Systems and methods for performing endometrial ablation," filed May 24, 2019.

Third Office Action issued by the Chinese Patent Office for Application No. CN 201780024406.5, dated Dec. 6, 2021 (Waiting for English Translation).

* cited by examiner

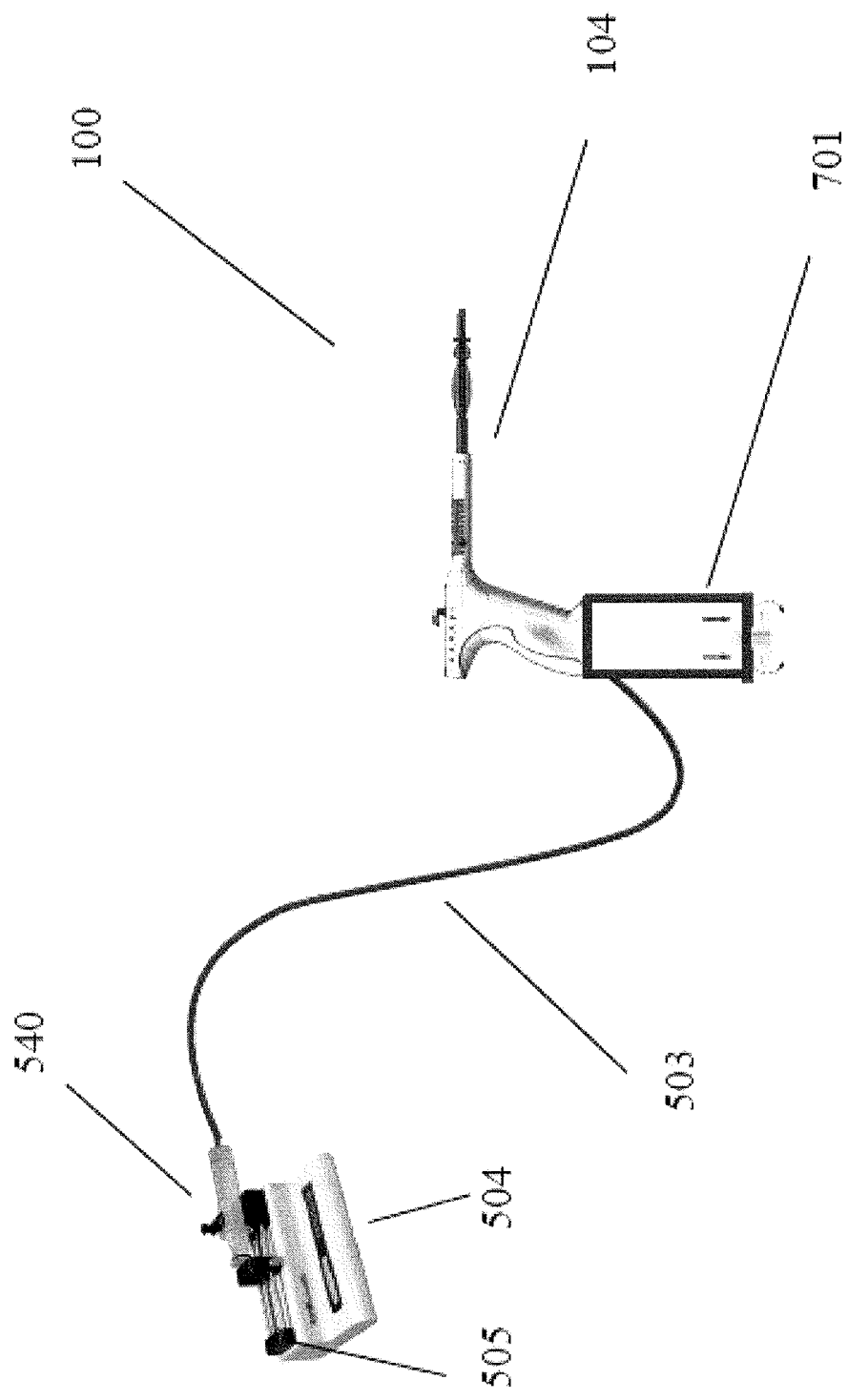

METHODS AND APPARATUS FOR DETERMINING THE INTEGRITY OF A BODILY CAVITY

CROSS REFERENCE TO RELATED APPLICATIONS

This application claims the benefit under 35 U.S.C. 119 of U.S. Provisional Patent Application No. 62/297,643, filed Feb. 19, 2016, titled "Methods and Apparatus for Determining the Integrity of a Bodily Cavity", and is a continuation-in-part of U.S. patent application Ser. No. 13/648,132, filed Oct. 9, 2012, titled "Integrity Testing Method and Apparatus for Delivering Vapor to the Uterus", both of which are incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD OF THE DISCLOSURE

The present disclosure generally relates to uterine procedures incorporating a distension media such as a fluid or a gas that could be used with endoscopic procedures or other visualization systems such ultrasound or fluoroscopy. The present disclosure is particular suited for endometrial ablation of the uterine lining but can be used for the treatment and inspection of system integrity would be useful in other bodily cavities such as the lung, urethra, bladder, and bodily lumens such as the esophagus, GI system, ureter, nasal airway, stomach, and arterial/venous/lymph systems. More specifically, the present disclosure relates to endometrial ablation with a heated vapor and specifically integrity and patency test systems that provide the physician user information on both the integrity of the bodily cavity being treated and the reliability of the initial integrity test result.

BACKGROUND

Endometrial ablation (i.e., the removal or destruction of the endometrial lining of the uterus) is used as an alternative to hysterectomy for treating menorrhagia, or other uterine diseases. One prior technique for performing endometrial ablation employs a resectoscope (i.e., a hysteroscope with a built-in wire loop or other ablative devices) that is inserted transcervically into the uterus, and uses radio-frequency electrical current (RF current) to remove or coagulate the endometrial tissue. These standard techniques typically are performed in a hospital setting and importantly utilize hysteroscopy for visualization of the procedure while treating the uterine lining.

Some approaches make use of heated fluid to ablate the endometrium. For example, early journal articles describe the use of steam to treat uterine hemorrhage. The use of steam for this purpose was later discredited, apparently due to patient morbidity and mortality. See, e.g., Fuller U.S. Pat. No. 6,139,571. More recent descriptions of the use of injecting hot fluid into the uterus have been described. Uterine therapies employing a contained fluid have also been described.

In an effort to simplify the procedure, approaches have been developed that do not require concurrent hysteroscopic visualization. In practice, many of these techniques recommend that the physician or user employ hysteroscopy to visualize and inspect the uterine cavity prior to performing the endometrial ablation procedure. In addition, hysteroscopy may be employed at the conclusion of the endometrial ablation procedure as a method to inspect the uterine cavity post treatment. During this hysteroscopic inspection, the physician is verifying that the uterine cavity is not perforated although perforations may not be readily apparent even with hysteroscopic visualization. In general, a physician seeks to avoid perforations for many reasons including the potential for unintended injuries to neighboring organs and maintaining or confining the treatment area to specifically the uterine cavity in the case of endometrial ablation procedures.

Endometrial ablation techniques that do not require active hysteroscopic visualization during treatment operation are commonly referred to as "blind" techniques since the physician is using tactile feel, or markers and indicia on the endometrial ablation device to indicate proper placement of the device in the uterine cavity. One of these particular devices utilizes a balloon-based system using ultrasound as the energy source. High frequency, or radiofrequency (RF), energy has also been used to perform thermal ablation of endometrial tissue. Current products for performing endometrial ablation include the NOVASURE® procedure and a system marketed under the trade name THERMACHOICE®, by Ethicon, Inc. of Somerville, N.J. Cryogenic ablation, or "cryoablation," such as HER OPTION® from American Medical Systems, Inc., is another endometrial treatment approach. All of the products above are characterized as "blind" or not requiring direct hysteroscopic visualization during the treatment.

In utilizing an endometrial ablation technology that does not require hysteroscopic visualization, it would be beneficial to employ a test to verify that the uterine cavity is intact or unperforated prior to performing the treatment. Such tests are referred to as uterine integrity tests and these tests can be performed with endometrial ablation procedures and any procedure of the uterus or hollow body cavity or organ. In addition, these tests can be used with hysteroscopic procedures since a perforation may not be readily detected even under direct vision.

Integrity tests employ saline or gas, preferably saline and specifically carbon dioxide gas, as agents to verify if the uterine cavity is intact in regards to holding fluid or gas pressure. The gas or fluid is supplied under pressure to the uterine cavity and a leak in the uterine cavity, whether it is a perforation, an unsealed cervical canal, or the effect of excess fluid exiting the fallopian tubes, can be discerned. Stern et al. (U.S. Pat. No. 5,562,720) and Sampson et al. (U.S. Pat. Nos. 6,554,780, 6,743,184, 6,872,183, and 7,063,670) describe such pressure techniques while other approaches check for fluid imbalances between an input source and output collection using volume measurements. Other approaches mention using flow rate and pressure measurements.

SUMMARY OF THE DISCLOSURE

A further improvement to the patency test is the real time control of the fluid flow rate. As an example, if the initial patency test result demonstrates a low or near threshold fluid flow rate, the fluid flow rate can be instantaneously increased in an attempt to unclog the lumen of the uterine ablation device. The lumen could be clogged with blood, tissue, or debris and this burst of increased fluid flow would be done in an attempt to free the lumen of the materials that are interfering with the patency test. If the increased fluid flow does not improve the flow rate in the patency test assessment, the uterine ablation device is removed from the patient and the device is inspected for clogging materials, and the entire process of the device insertion, with integrity and subsequent patency testing, is initiated. However, if the increased fluid flow is successful in removing the clogging materials in situ, the uterine cavity integrity test can repeated, with a subsequent confirmatory patency test, without the need for device removal and reinsertion. In this instance, the successful application of increased fluid flow resulted in less procedure time, less risk to the procedure, and patient discomfort by removing the need for device removal and reinsertion.

In practice, the integrity and patency tests can be improved by the incorporation of additional mechanisms that would remove the requirement for specifying or establishing the height differential between the height of an elevated saline bag above the uterus to supply a saline irrigation source. Especially as it relates to the changing water level as the source of irrigation fluid becomes depleted during a procedure.

Further improvement to the accuracy and ease of applying the integrity system would be a benefit to the physician user, or making the entire system less expensive by the removal of accessory components that have been required in previously disclosed systems. The described systems demonstrate an improved integrity and patency test systems that either remove the requirement of an internal pressure sensor or an integrated flow meter within the system.

Also in practice, a system in which controlling the actual flow rate within the integrity and patency test system provides new benefits to the system that make the entire test more robust and accurate.

In another embodiment, the system utilizes a pressurized fluid reservoir within a handle of a uterine insertion device that is configured for delivering a therapeutic agent to the uterine cavity, such as a handle for delivering vapor independent of patient height relative to the fluid source and thus requires no patient height measurement prior to performing the integrity test. An air pressure regulator is used to set the fluid or liquid pressure within a small reservoir, and the fluid level in the reservoir is controlled or kept at the appropriate level or threshold by a fluid supply system. One or more sensors in the reservoir is used to measure a fluid level. As the fluid level in the reservoir goes down, the fluid supply system injects more fluid into the reservoir and ceases to place fluid in the reservoir when the threshold or fluid level is reached. The fluid supply system measures the flow rate as it supplies fluid into the reservoir.

Alternatively, the time to reach a threshold is monitored to estimate the flow rate. Fluids used are liquids such as saline, water, distilled water, etc.

In one embodiment the fluid supply system is a stepper motor, syringe pump, or gear pump that drives a syringe plunger to create a syringe pump and the one or more sensors are an infrared sensor(s) that monitor the fluid level in the small reservoir.

Additional embodiments and system elements that can be used separately or in combination for performing both an integrity and a subsequent patency test are described herein.

A method of performing an integrity test for a uterus of a patient is provided, comprising the steps of inserting a uterine ablation device into the uterus of the patient, activating a fluid supply system to deliver fluid into a reservoir disposed on or in the uterine ablation device, deactivating the fluid supply system when a fluid level in the reservoir reaches an upper threshold, pressurizing the fluid in the reservoir with a pressure source acting through a pressure regulator to deliver fluid from the reservoir of the uterine ablation device into the uterus, monitoring the fluid level of the fluid in the reservoir with one or more sensors of the reservoir, re-activating the fluid supply system when the fluid level in the reservoir reaches a lower threshold, and determining if there is a leak in the uterus based on a flow rate of the fluid supply system.

In one embodiment, the reservoir is opened to atmosphere prior to the activating step.

In another embodiment, the reservoir is closed to atmosphere after the deactivating step.

In some embodiments, it is determined that there is not a leak in the uterus if the flow rate of the fluid supply system falls below a flow rate threshold for a predetermined time. In one embodiment, the flow rate threshold is 5 mL/min and the predetermined time is 15 seconds.

In another embodiment, it is determined that there is a leak in the uterus if the flow rate of the fluid supply system does not fall below a flow rate threshold for a predetermined time over the course of an integrity testing time limit. In one embodiment, the flow rate threshold is 5 mL/min, the predetermined time is 15 seconds, and the integrity testing time limit is 60 seconds.

In some embodiments, the one or more sensors comprise infrared sensors, contact sensors, magnetic sensors, or ion sensors.

In one embodiment, the pressure source is pressurized to 55 mmHg.

In another embodiment, a pressure in the uterine cavity is independent of a patient height relative to the pressure source.

A uterine treatment device is provided, comprising a shaft sized and configured for insertion into a uterus of a patient, inflow and outflow lumens disposed along a length of the shaft, at least one inflow port disposed at a distal end of the inflow lumen, at least one outflow port disposed at a distal end of the outflow lumen, a fluid reservoir operatively coupled to the inflow and outflow lumens, one or more sensors configured to monitor a fluid level in the fluid reservoir, a fluid supply system connected to the fluid reservoir, the fluid supply system being configured to deliver fluid into the fluid reservoir, a pressure source connected to the fluid reservoir, the pressure source being configured to pressurize fluid in the fluid reservoir to deliver fluid from the reservoir into the uterus of the patient, a pressure regulator disposed between the pressure source and the fluid reservoir, the pressure regulator being configured to reduce a pressure from the pressure supply to a predetermined pressure value, and a controller configured to activate the fluid supply system to deliver fluid into the fluid reservoir and deactivate the fluid supply system when the fluid level reaches an upper threshold, the controller being further configured to determine if there is a leak in the uterus based on a flow rate of the fluid supply system.

In one embodiment, the controller is configured to determine that there is not a leak in the uterus if the flow rate of the fluid supply system falls below a flow rate threshold for a predetermined time. In another embodiment, the flow rate threshold is 5 mL/min and the predetermined time is 15 seconds.

In one embodiment, the controller is configured to determine that there is a leak in the uterus if the flow rate of the fluid supply system does not fall below a flow rate threshold for a predetermined time over the course of an integrity testing time limit. In one embodiment, the flow rate threshold is 5 mL/min, the predetermined time is 15 seconds, and the integrity testing time limit is 60 seconds.

BRIEF DESCRIPTION OF THE DRAWINGS

FIG. 11 illustrates a further embodiment utilizing a pressure relief valve.

DETAILED DESCRIPTION OF THE INVENTION

Figure 1A:
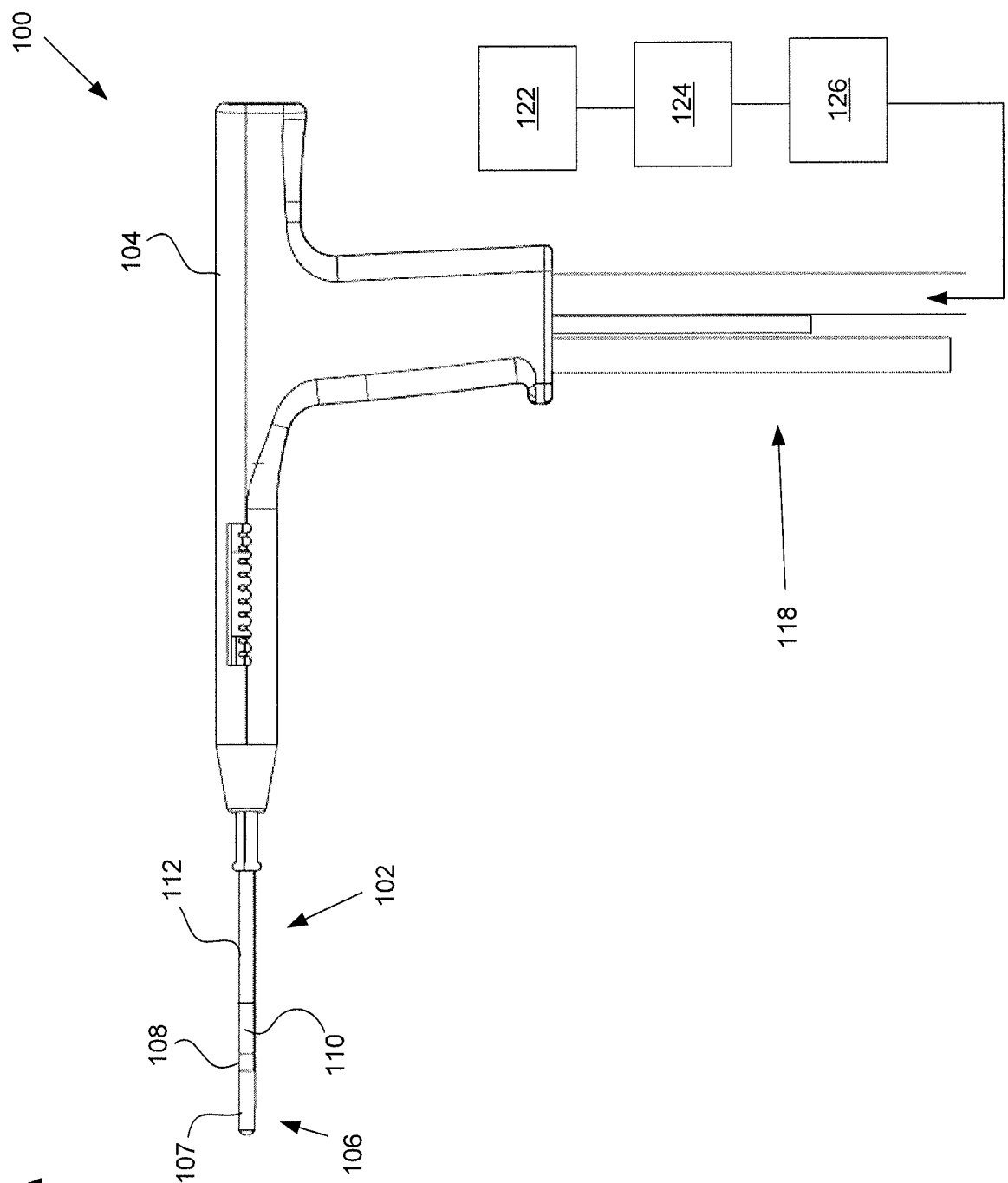
FIGS. 1A-1B illustrate one embodiment of a uterine ablation device.

FIG. 1A illustrates a uterine ablation device 100 sized and configured to access the endometrium of a uterus and to deliver a heated vapor to the uterus to ablate uterine tissue. The device can be configured to ablate and treat the endometrial lining of the uterus as an alternative to hysterectomy for treating menorrhagia or other uterine diseases. In some embodiments, the device 100 can be configured to gain access to the uterus by being inserted through a cannula or hysteroscope. The device 100 can include shaft 102, handle 104, distal tip 106, vapor ports 107, distal anchor or distal balloon 108, central or sealing balloon 110, proximal or positioning balloon 112, and connection lumens 118, which can couple the uterine ablation device to a control system (not shown) comprising a computer, a vapor generation system, and mechanisms configured to inflate and deflate the balloons as well as control the delivery and removal of integrity gas/fluid and vapor from the device. Additionally, connection lumens 118 can connect device 100 to a gas/fluid source 122, pressure regulator 124, and flow meter(s) 126. Vapor ports 107 near the distal tip 106 of the device can be fluidly coupled to the connection lumens 118 via inflow and outflow lumens (not shown). The vapor ports, inflow and outflow lumens, connection lumens, gas/fluid source, pressure regulator, and flow meters can be configured for testing the integrity of the patient's uterus, proper placement of the device, and verifying the presence of flow between the inflow and outflow lumens of the device.

The flow meter can be any flow meter as known in the art, including a thermal mass flow meter, an ultrasonic flow meter, a paddlewheel, or a variable area flow meter. In one embodiment, an ultrasonic flow meter that utilizes transit time and Doppler flow readings is advantageous since it is a non-contact system that does not need to physically interact with the fluid or gas media being employed in the integrity test. An ultrasonic flow meter can be easily adaptable to the exterior dimensions of an inflow lumen. In addition, a drip chamber within the inflow lumen can be used to manually visualize or record drips or flow from the fluid source as the integrity test indicates a sealed uterine cavity. In some uterine procedures, it may be advantageous to use other types of fluid besides saline including Lactated Ringers, non-isotonic solutions for certain electrosurgical procedures, gels, foams, fluids of varying viscosity for some ultrasonographic procedures, or other fluids used in uterine procedures.

In one embodiment, a one way valve can be placed in the inflow lumen just distal or past the flow meter from the gas/fluid source. The one way valve can allow for the flow of gas/fluid (e.g., saline) from the gas/fluid source to the device and uterine cavity. The one way should not interfere with the operation of the flow meter and its readings. In operation, the uterine cavity is a muscle that can undergo significant contractions in the presence of uterine distension or when the uterine cavity is filled with gas/fluid, and in particular a fluid such as saline. These contractions can push the fluid retrograde back through the saline lumen and past the flow meter. In doing so, flow meter measurements can become difficult to interpret or may produce sinusoidal waves in the output readings. The placement of the one way valve in this location can eliminate retrograde fluid flow and stabilize readings for the flow meter during episodes of uterine contractions.

Handle 104 can be an ergonomic handle and can include features and controls for using the device (e.g., buttons, levers, indicia for providing feedback for depths of insertion, valves, etc.), including features for controlling inflation of balloons 108, 110, and 112, and for controlling the delivery and removal of integrity test gas/fluid and heated vapor from the device. The handle can also include features and controls for testing the integrity of the patient's uterus, proper placement of the device and verifying the presence of flow between the inflow and outflow lumens of the device.

The balloons described herein can be any type of flexible balloon, such as rubber, latex, urethane, silicone, PET, LDPE, parylene, nylon, PE, combinations of these polymers, or can be manufactured from any other suitable material as known in the art. It should be noted that in some embodiments, the distal anchor comprises a balloon, but in other embodiments, the distal anchor comprises an expandable anchor or expansion mechanism, such as expandable frames, filters, nets, or cages, or non-expandable components that increase the diameter of the shaft of the uterine ablation device. For purposes of this disclosure, however, the distal anchor may be referred to as a distal anchor or as a distal balloon.

Shaft 102 can be configured to deliver a heated vapor from a remote boiler (not shown) through the device and out of vapor ports 107 in distal tip 106. The shaft can also be configured to return vapor that has exited the device, including bodily fluids, uterine materials, and condensate back through the vapor ports and into the shaft. In FIG. 1A, vapor ports 107 are illustrated as including both the vapor delivery and vapor return ports. However, in other embodiments, the vapor delivery ports can be separate and distinct from the vapor return ports. For example, vapor delivery ports are intended to provide an even distribution of heated vapor through a cavity, and may comprise small lumens or holes on the end of the shaft. The vapor return ports, in contrast, are intended to return used vapor and condensate, and may comprise larger slots to prevent blood, tissue, etc. from blocking or clogging the return lumen. The device comprises inflow and outflow gas and/or fluid delivery channels to conduct uterine integrity and patency tests. In some embodiments, the lumens to deliver and return vapor are the same as the channels to deliver and return gas and/or fluid for the uterine integrity and patency tests.

Referring still to FIG. 1A, uterine ablation device 100 is shown in a collapsed delivery configuration, with distal balloon 108, sealing balloon 110, and positioning balloon 112 deflated to reduce the cross sectional diameter of the device and can be 6 mm in diameter during insertion or smaller. When the device is in the delivery configuration, the reduced profile allows for easier access through the vagina, cervical canal, and cervix to gain access to the uterus, and provides reduced patient discomfort during insertion. In some embodiments, the outer dimensions of the uterine ablation device are such that introduction of the device into the uterine cavity can be achieved without the need for mechanical or pharmacological dilation of the internal cervical os prior to device introduction.

Figure 1B:
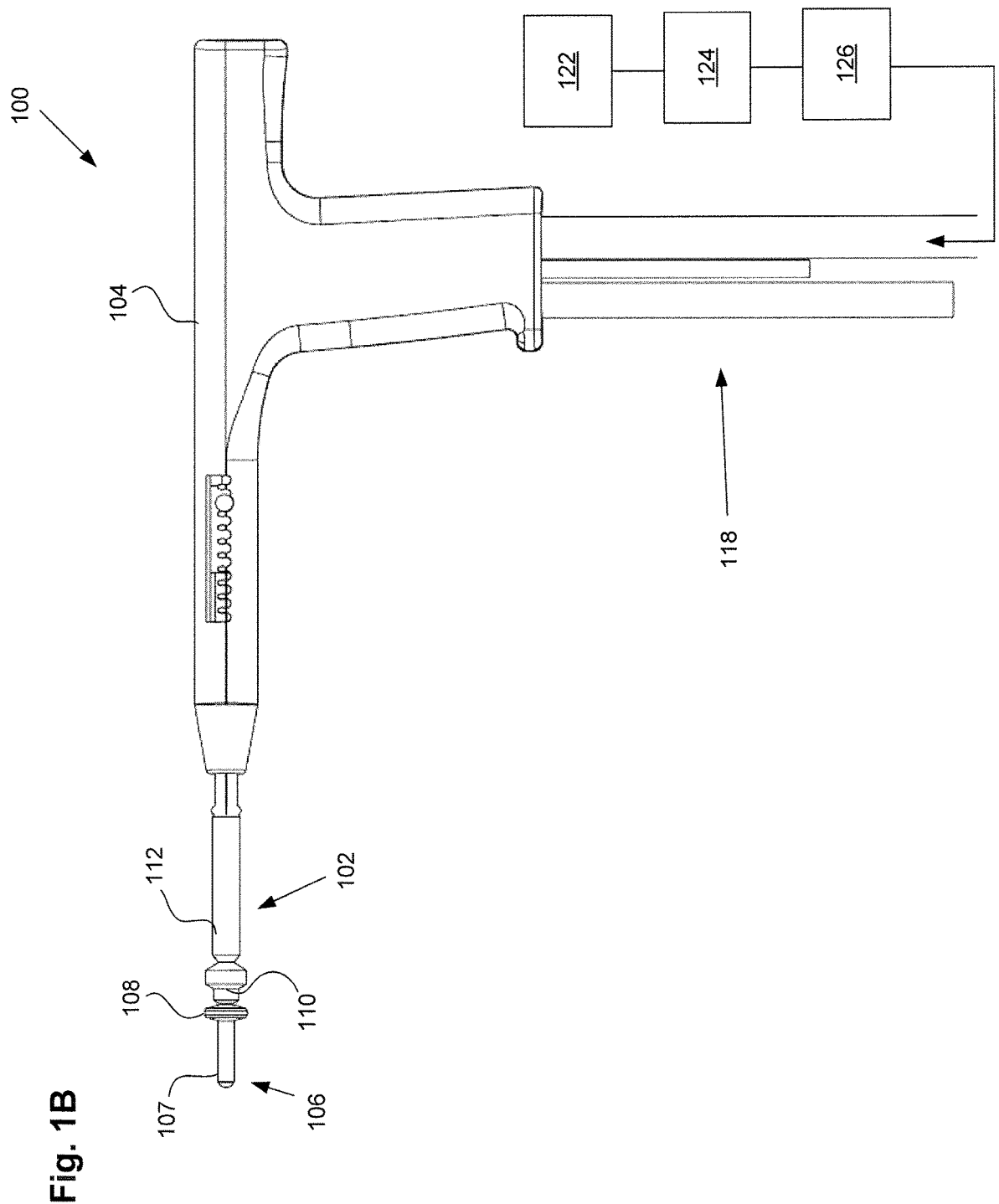

FIG. 1B illustrates the uterine ablation device 100 of FIG. 1A with all three balloons inflated, including distal balloon 108, central sealing balloon 110, and positioning balloon 112. The central balloon can be inflated with a fluid, such as saline, or alternatively, can be inflated with air. Although three balloons are depicted in FIG. 1B, in other variations one, two, four, or more balloons may be provided, and other balloon shapes may be used. The positioning balloon can be inflated with a room temperature medium, a cooled medium, or alternatively, a heated medium. In some embodiments, the central sealing balloon comprises a length along shaft 102 of approximately 15 mm to 25 mm. The central balloon can be disposed on the shaft between the distal balloon or anchor and the proximal balloon. In some embodiments, the central balloon is adjacent to both the distal balloon and the proximal balloon. In other embodiments, there is a small gap or space between one or more of the balloons. The length and position of the central balloon on the shaft ensures that when inflated, the central balloon seals the cervix off from the uterus near the internal cervical os, but the balloon does not extend into the uterus or into the vagina of the patient. The central and proximal balloons can comprise any diameter, but preferably should have a diameter large enough to be able to engage the walls of the cervix in the average female patient. For instance, the central balloon may have an inflated outer diameter of 10 mm and accommodate 9.5 psi of pressure in actual use. The proximal balloon can have a larger diameter, such as 17 mm and a lower inflation pressure of 7 psi.

Placement of the ablation device of FIGS. 1A-1B will now be described. The distal tip of the ablation device can be inserted past an external os into the cervical canal of the patient, and past an internal os of the patient to gain access to the uterus. In one embodiment, the distal balloon can be positioned within the uterus distal to the internal os, the sealing balloon can be positioned at or proximal to the internal os and extending into the cervical canal, and the positioning balloon can be positioned within the cervical canal and extending proximally into or towards the vagina.

Once the distal tip of the ablation device is disposed within the uterus, just distal to the internal os, the distal balloon can be inflated to the desired pressure. In some embodiments, the balloon can be inflated to a pressure of up to approximately 20 to 30 psi so as to prevent accidental withdrawal of the ablation device from the uterus. It should be noted that at this point, the distal balloon is positioned slightly past the internal os of the cervix. Inflation of the distal balloon can later serve as an anchor to prevent the device from sliding proximally out of the uterus.

Figure 2:
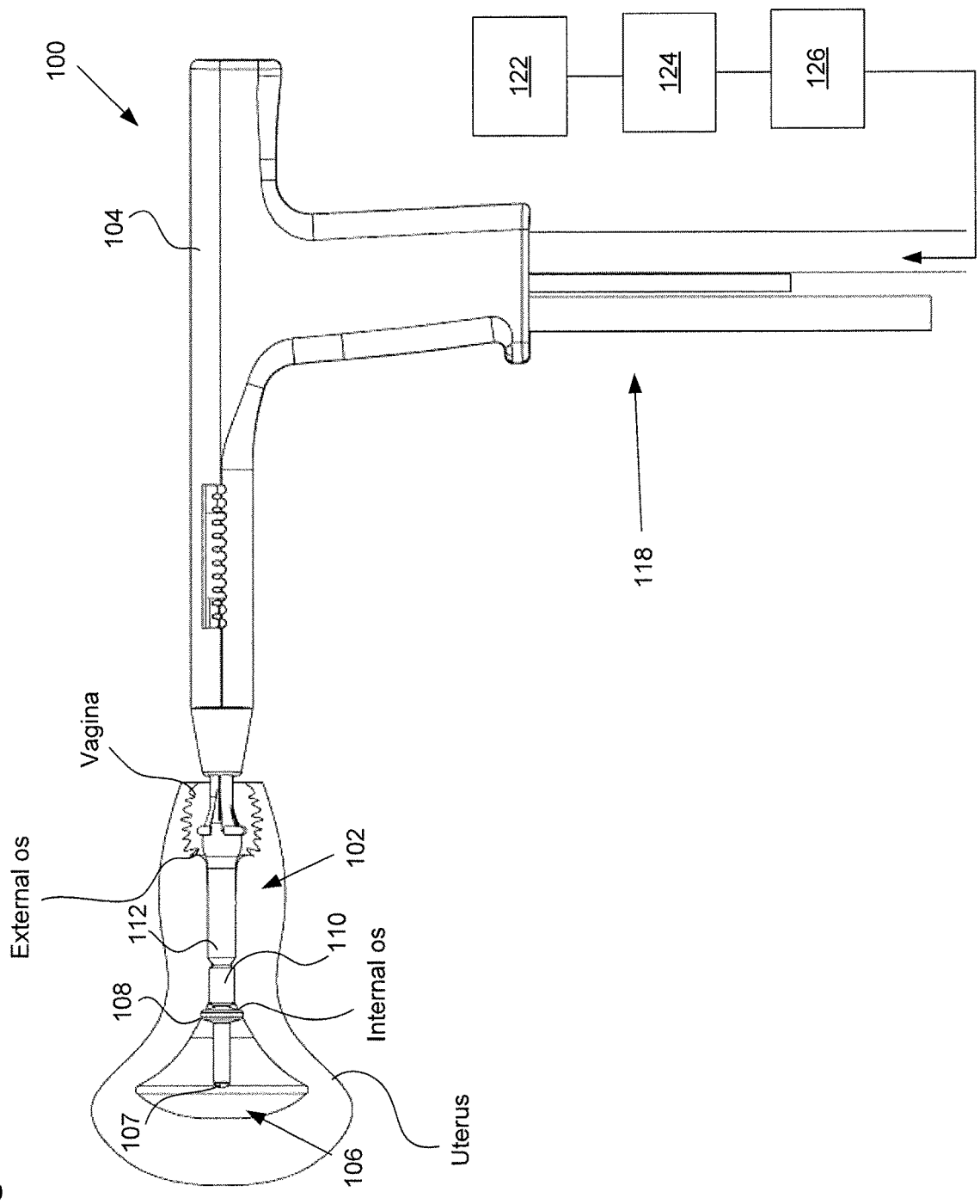
FIG. 2 illustrates an integrity test of the uterine ablation device.

After inflating the distal balloon, the proximal balloon can be inflated to cause the device to assume a positioned configuration, with the distal balloon fully seated against the internal os and the positioning or proximal balloon expanded within the cervix and extending past the external os into the vagina. As the proximal balloon is inflated, the balloon can expand outwardly from the cervix into the relatively unconstrained space of the vagina, which creates a compression force that pulls the device and the distal balloon proximally to engage against the interior portion of the internal os (also known as the cervical ostium or cervical os). FIG. 2 illustrates ablation device 100 inserted into the uterus of a patient with balloons 108, 110, and 112 inflated as described above.

After positioning the ablation device but prior to delivery of vapor, it can be advantageous to assess the integrity of the uterus to test that the vapor delivery tip of the device is positioned within a sealed uterus and to test that there is flow between the inflow and outflow lumens, by performing an integrity test and a patency test. The amount of fluid and rate in which it flows into the uterine cavity can provide the physician an indication of the size of the uterine cavity and whether the device is in a false passage. An integrity test can assess that the uterus is sealed, and determine leaks originating from 1) perforations to the uterine wall, or 2) leaks from inadequate sealing at the cervix or leaks from the fallopian tubes.

A second test that made an assessment for patency, referred to as the device lumens patency test or patency test, could provide an indication to the physician whether the device was clogged with debris or within a false passage. This additional information to the physician, in conjunction with the integrity test, could provide greater assurance to the physician of device location during "blind" endometrial ablation procedures.

In clinical use, a uterine integrity and patency test could be useful for additional uterine procedures besides uterine ablation procedures such as the implantation of a device, implant, or a diagnostic or therapeutic agent. In these cases, a separate unit or module that can conduct a uterine integrity and patency test, sequentially, separately, or individually, with a separate uterine cavity introducer can be employed without a uterine ablation device or system.

In one embodiment, a uterine integrity test can contain the following elements and steps. Referring to FIGS. 1A-1B and FIG. 2, gas/fluid source 122 can be connected to pressure regulator 124 comprising either one regulator or an additional back pressure regulator. The gas/fluid source can contain a gas, such as $CO_2$, or inert gases, or a fluid, such as saline, Ringer's Lactate, non-isotonic solutions, glycerine, sterile water, and mineral oil for example. The regulator 124 is configured to keep the pressure of the external gas source below a safety threshold value. In one embodiment, the safety threshold value can be approximately 70 mm Hg. The actual pressure amount or graduation may not be monitored and may not need to be. The fluid or gas from gas/fluid source 122 can be driven at a constant pressure bounded by the safety threshold value (e.g., can be bounded by the maximum pressure the uterus will see during treatment, such as 70 mm Hg). In addition, it can be useful to operate a uterine integrity test at a pressure equal to higher than the pressure required for conducting the endometrial ablation or other uterine procedure.

In use, gas/fluid pressure can be achieved by elevating the gas/fluid source a height distance above the uterine cavity to create pressure. This height elevation can be verified by a measuring stick, tape or laser. An example of a clinically used height for a saline bag would be 32 inches above the height of a patient's uterus. At this height, the pressure would be between 50 and 70 mmHg. This pressure is low enough to be below the reported opening pressure of the fallopian tubes. In addition, a pressure sensor within the uterine cavity can verify that the appropriate amount of pressure is being applied for the integrity test and patency tests. A self-adjusting feedback mechanism can be employed to raise or lower the pressure of the saline source in response to pressure measurements taken from within the uterine cavity before the integrity and patency tests are run. As an example, this feedback mechanism can raise or lower the height of the saline source in response to the pressure measurements taken from within the uterine cavity.

Alternatively, the uterine integrity test can be conducted by detecting a flow rate of the distal lumen of the uterine device or uterine ablation device under known conditions to determine the proper pressure or height of the gas/fluid source. For instance, flow rate readings can be taken while the gas/fluid source is at a certain height and the uterine device maintained within a known condition or in free space. As the height of the gas/fluid source is raised or lowered, the flow rate of the gas/fluid will respond accordingly until the gas/fluid source is placed at a height at the desired flow rate, or is pressurized to the desired amount. Likewise, the gas/fluid source can be raised or lowered by a self-adjusting feedback mechanism in response to the measured flow rate.

In some embodiments, the uterine ablation device can further include a flow meter 126 having a read out mechanism (not shown) to the end user. In some embodiments, the flow meter is disposed near distal tip 106 of the device. In other embodiments, the flow meter can be disposed within an outflow lumen of the device (not shown). In yet another embodiment, the flow meter can be disposed external to the device but along the flow path between gas/fluid source 122 and the ablation device. The flow meter can be configured to measure and report a flow rate of fluid/gas or vapor through the uterine ablation device. The read out mechanism can be numerical, graphical, or icon based. Other variations include various audio and visual signals, indicia, qualitative indicia, alarms, and color identifiers. A filter may or may not be attached to the flow meter.

Figure 3:
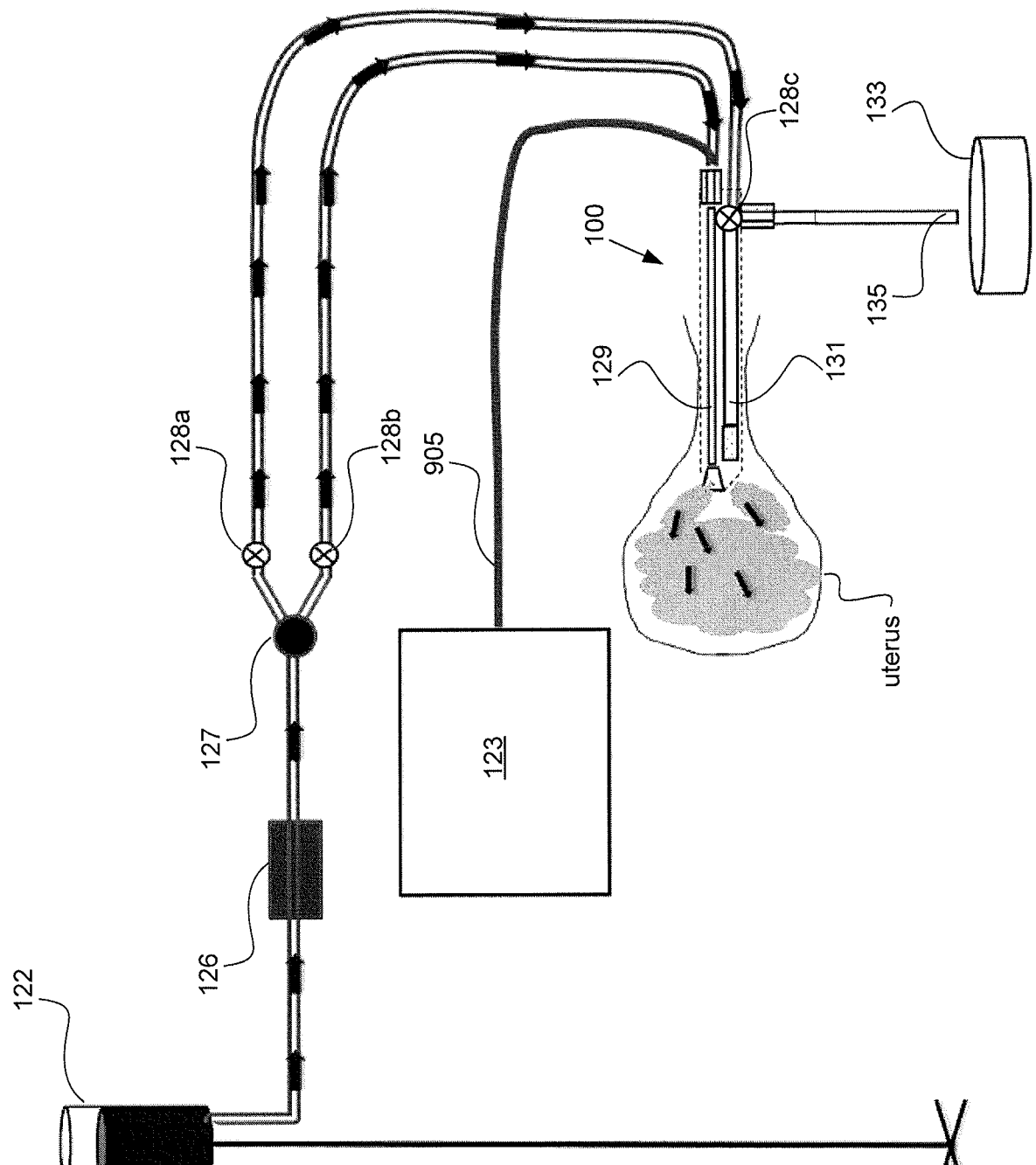
FIG. 3 illustrates one configuration of an apparatus during a uterine integrity test.

Referring to FIGS. 2 and 3, to perform a uterine integrity test, gas, such as $CO_2$, or a fluid, such as saline, can be delivered from the gas/fluid source 122, through the pressure regulator 124, and through the flow meter 126 into the uterine ablation device 100. As shown in FIG. 3, the gas/fluid can be delivered into the uterus via both inflow lumen 129 and outflow lumen 131.

In one embodiment, a one way valve 127 as seen in FIG. 3 can be located between the flow meter 126 and the uterine ablation device 100. In other variations the one way valve 127 can be located in the handle of the uterine ablation device 100 as well as other components such as the flow meter 126 and valves 903. The one way valve can reduce or eliminate retrograde flow of saline during uterine contractions. The one way valve is characterized as providing low resistance to flow in one direction (towards the uterine cavity) and high resistance to flow in the retrograde direction (towards the gas/fluid source). Advantageously the one way valve can stabilize flow values because retrograde flow values are eliminated. By reducing the sinusoidal wave patterns that can be caused by uterine contractions or relaxations, movements by the patient, or inadvertent manipulations of the inflow line or the patient herself by the physician or medical staff, the procedure time is reduced. This filtering out of negative flow values isolates positive components of flow, reduces noise in flow rate values, thereby accelerating the interpretation of flow rate data and reducing procedural time.

A controller of the uterine ablation device (not shown) can be configured to open and close valves 128a, 128b, and 128c to allow gas or fluid to flow from source 122 into the inflow and outflow lumens 129 and 131 of the ablation device 100. During a uterine integrity test, the controller can be configured to open valves 128a and 128b and close valve 128c. This allows gas or fluid to flow from source 122, through flow meter 126, through one way valve 127 and valves 127a and 128b, and into inflow lumen 129 and outflow lumen 131. As the gas or fluid enters the uterus, the flow meter can measure an integrity flow rate of the gas or fluid. If the flow rate decreases below an integrity flow rate threshold value, the controller can determine that the uterus is sealed. In some embodiments, this integrity flow rate threshold value can be approximately 5 ml/min.

The gas/fluid can exit vapor ports 107 of the device and enter the uterine cavity. These exit vapor ports can also be referred to as the fluid infusion tip and fluid outflow tip. As described above, for the integrity test, both the inflow and outflow lumens of the uterine ablation device can be utilized to provide fluid/gas to the uterine cavity. As the pressure in the uterus increases, the flow of fluid or gas through the uterine ablation device should decrease to a value of zero or to a value below an integrity flow rate threshold value, which occurs when the pressure in the uterus equals the drive pressure of the system. Utilizing both the inflow and outflow lumens for the flow of the gas/fluid during insertion of the device into the patient can help prevent the vapor ports from becoming clogged or blocked during insertion.

For the patency test, the inflow lumen can be utilized for gas/fluid flow into the uterus while the outflow lumen is used for the return of gas/fluid from the uterus.

For the integrity test, by measuring the flow of gas or fluid into the uterus with flow meter 126, and more specifically, by measuring a declining flow rate of gas/fluid into the uterus or a steady state flow rate in the uterus, the system or a user can determine the state of the uterus and correct positioning of the device in the uterus. For example, 1) if the flow rate does not decrease or decreases to a flow rate higher than a threshold flow rate, for example 5 ml/min, then there is either a leak in the uterus or the device, or the device is not positioned properly within the uterus; 2) if the flow rate drops to zero immediately, then the distal tip of the uterine ablation device may be clogged or embedded in the tissue; 3) if the flow rate drops to a level above zero and stays there (e.g., ~30 mL/min), then a small leak may be present. The size of the leak can be proportional to the measured flow rate; 4) if the flow rate oscillates between a low level and a high level, then a hole or leak may be present which is sealed or closed at lower pressures but opens at higher pressures; and 5) if the flow rate drops below a threshold value or to zero within a certain time limit, bounded by both min and max time, then the device is positioned correctly within a sealed uterus. In one embodiment, a min and max time to determine proper positioning within a sealed uterus can occur within a test window of 10 to 60 seconds with a 15 second window being preferred. The flow rate threshold can be set at a numerical value of 5 ml/min wherein flow rates dropping below 5 ml/min within the time window can be used as the threshold for a sealed uterine cavity and greater than or equal to 5 ml/min as the threshold for detecting a leak or an unsealed uterine cavity. The numerical value of 5 ml/min as a sealed or unsealed threshold for integrity testing has been shown to be effective for the uterine ablation device utilizing vapor. Intentionally made perforations in test uteri were demonstrated to not allow vapor to traverse the perforation at values less than 5 ml/min. The establishment of a threshold value for sealed or unsealed uterine cavity must take into account the resolution limitations of the flow sensors and meters, and the rate of saline absorption in the uterine cavity.

In analyzing integrity test data for leak or non-intact thresholds, empirical testing demonstrated that there is a statistically significant difference between tests determined as "pass" (flow <5 ml/min) or "fail" (flow >5 ml/min). The average minimum change in saline flow rate and maximum saline flow rate are significantly different, indicating that the integrity test can effectively discern between leaks and absence of leaks in a test environment where perforations are intentionally applied to a test uterine cavity as shown in the table below. This statistically significant difference improves further when negative flow values are eliminated with the use of a one way valve ($p<0.001$ for Min Δ flow and $p<0.001$ for Max flow). Based on this analysis, a 5 ml/min integrity test threshold for leak detection can be established and applied for clinical use. In addition, an algorithm to analyze the data automatically can be developed for its ability to determining uterine integrity.

TABLE 1

Uterine Cavity Integrity Test Results in Test Uteri with Intentionally Created Perforations:

| | Flow data as recorded | | No negative flow values | |
|---|---|---|---|---|
| | Min Δ flow | Max flow | Min Δ flow | Max flow |
| Uterine Cavity Integrity Tests Declared as "NOT SEALED" (n = 12) | | | | |
| Average | 10.42 | 8.75 | 10.42 | 11 |
| Standard Deviation | 4.38 | 15.55 | 4.3 | 12.64 |
| Maximum | 17 | 38 | 17 | 38 |
| Minimum | 2 | −15 | 2 | 0 |
| Uterine Cavity Integrity Tests Declared as "SEALED" (n = 41[1]) | | | | |
| Average | 3.12 | 2.34 | 3.12 | 2.41 |
| Standard Deviation | 2.19 | 2.17 | 2.19 | 2.07 |
| Maximum | 8.00 | 6.00 | 8.00 | 6.00 |
| Minimum | 0.00 | −1.00 | 0.00 | 0.00 |

In Table 1, Min Δ flow refers to the minimum change in flow rate over a 15 second window of flow, shown in ml/min. Max flow refers to the maximum flow rate observed in a 15 second window of flow, shown in ml/min. No negative flow values refer to data points where only positive flow rates are calculated. Negative flow values will not occur with a one way valve in place.

As another consideration, the size and or shape of the uterus will likely change during the integrity test. Thus, in some embodiments, an average flow rate can be used to determine the integrity of the uterus or the positioning of the device. For example, in one embodiment, if the average flow rate over a predetermined time period, such as 5 seconds, is zero or lower than a threshold flow rate, then the uterus is likely sealed. In another variation, a 15 second time window can be taken in which the trailing average of data points is tabulated for every 15 second time increment. Other time window increments can be utilized as a standard for data collection.

In some embodiments, the return channel comprises a valve 128c, such as a solenoid valve, that can be activated upon the start of the integrity test to close off the egress of the gas/fluid through the return channel. Alternatively, a one way pump can be utilized. When the return flow of gas/fluid through the return channel is stopped with the valve, a change of flow can be detected by the flow meter 126 on the input line. In addition to determining if there is a leak or if the device is positioned properly, the specifics of the changes in flow (e.g., how the flow reacts to closing of the return line with the valve) can provide the following the indications in some cases: a) The size of the uterine cavity; and b) The presence of a leak or lack of integrity in the system. For instance in clinical use with uteri of varying sizes, an integration under the graphical curve of flow rate versus time provides a volume assessment of the size of uterine cavity. The amount of volume can provide the physician information not only on the size of the uterus, but whether the device is improperly embedded in a false passage (smaller volume amount) or in the peritoneal cavity (larger volume amount).

Figure 4:
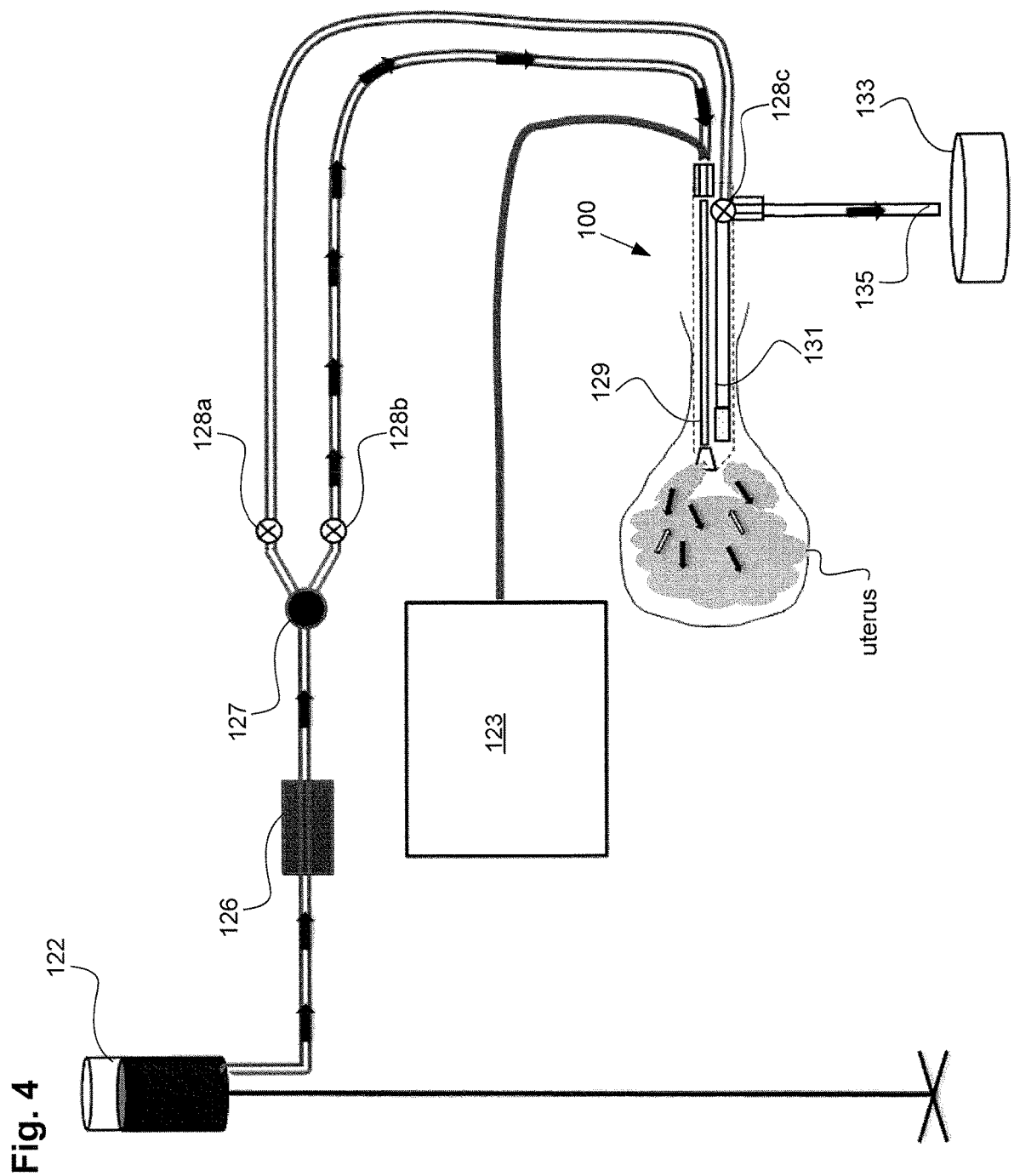
FIG. 4 illustrates one configuration of an apparatus during a uterine patency test.

Referring to FIG. 4, in some embodiments the amount of flow in the inflow and outflow channels can be used to determine the presence of an obstruction that may affect the flow of vapor during the ablation procedure. Based on this determination or patency test, the device may be repositioned or replaced prior to delivery of vapor. For example, in one embodiment, still referring to FIG. 4, a method of performing a patency test can comprise delivering gas or fluid from inflow lumen 129 of the uterine device into the uterus, also referred to as the fluid infusion tip, removing gas or fluid from the uterus with outflow lumen 131 of the uterine device, also referred to as the fluid outflow tip, and determining that the uterine device is not clogged or embedded in tissue if a flow rate of gas or fluid is observed in the flow meter of the inflow lumen of the uterine device. In FIG. 3 and FIG. 4, valves 128a and 128b control the flow of gas/fluid to the uterine ablation device 100 and valve 128c control the flow of gas/fluid from the outflow lumen 131 into the outflow canister or waste container 133. Control of the valves 128a and 128b and 128c can be performed by a separate controller and software unit shown as 123.

If it has been determined that the uterus is sealed based on the integrity test performed and described in FIG. 3, the controller can also be configured to perform a patency test. In one embodiment, referring to FIG. 4, the controller can be configured to open valves 128b and 128c, but close valve 128a. This allows gas or fluid to flow from source 122, through flow meter 126, through one way valve 127 and valve 128b, and into inflow lumen 129. Gas or fluid can be removed through outflow lumen 131, through valve 128c, and into a waste container 133 via tubing 135. As the gas or fluid enters and is removed from the uterus, the flow meter can measure a patency flow rate of the gas or fluid. If the patency flow rate is maintained above a patency flow rate threshold value, the controller can determine that the device is not clogged or embedded into tissue. In some embodiments, observing or measuring a flow of fluid or gas in outflow lumen 131 can be used to determine that the device is not clogged or embedded in tissue.

The patency test can also be revised with either the pressure driven or the flow driven systems. For example, if the distal end of the uterine ablation device was submerged or clogged with blood, tissue, or debris, a higher flow rate or pressure could be delivered to clear the distal end of the uterine ablation device to remove the source of clogging. This higher flow/pressure could be maintained or it could then be dropped down to a lower value during the patency test. Importantly, the requirement for applying a higher flow rate, or a higher pressure, to relieve clogging, may necessitate the repeat demonstration of integrity followed by a subsequent application of the patency test.

In empirical laboratory testing, it was demonstrated that the presence of blood and tissue within the lumens of a uterine device could provide a false result of uterine cavity integrity when measuring the flow rate of either a gas source, or a fluid source, through the uterine device. In such instances, the subsequent patency test demonstrated that the integrity test result was a false positive and the user would be alerted to a failed patency test and the procedure would not be allowed to continue to uterine cavity ablation. The accumulation of blood and tissue within lumens of uterine devices can occur during insertion or when the distal end of the uterine device is embedded within the tissue wall. This is particularly important for uterine ablation procedures since this patient population is characterized by active or uncontrolled bleeding, and uterine abnormalities that could contribute to greater amounts of lush endometrium or tissue, blood and clots, and loose debris or tissue within the uterine cavity. Underlying disease such as the presence of fibroids, myomas, or polyps that are often encountered in patients with abnormal bleeding also contributes to challenging anatomical configurations that makes the insertion and placement of uterine devices difficult and increase the risk of clogged lumens within uterine devices.

Figure 7A:
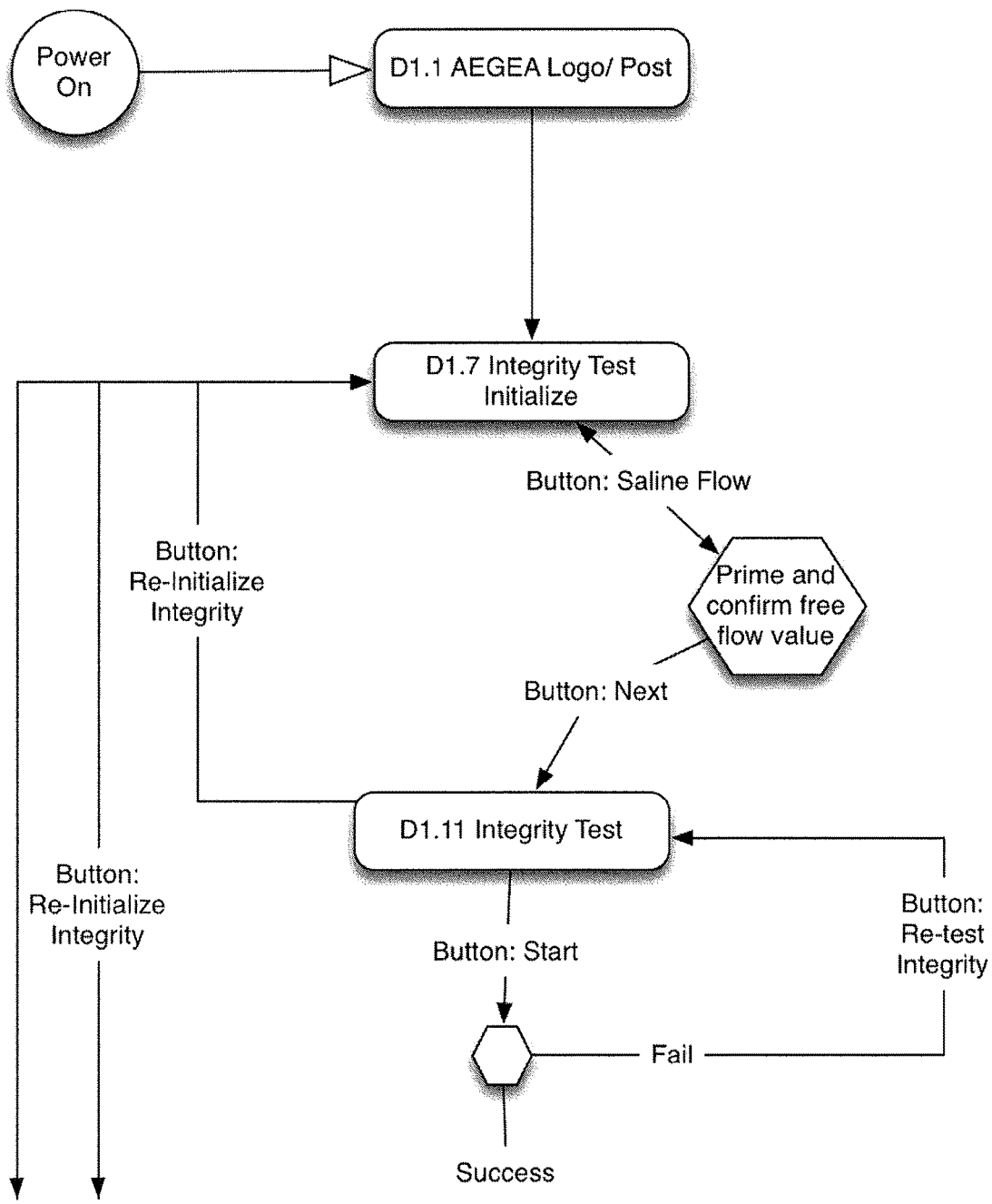
FIGS. 7A-7B illustrate an algorithm for one configuration of a uterine integrity and patency tests.
Figure 7B:
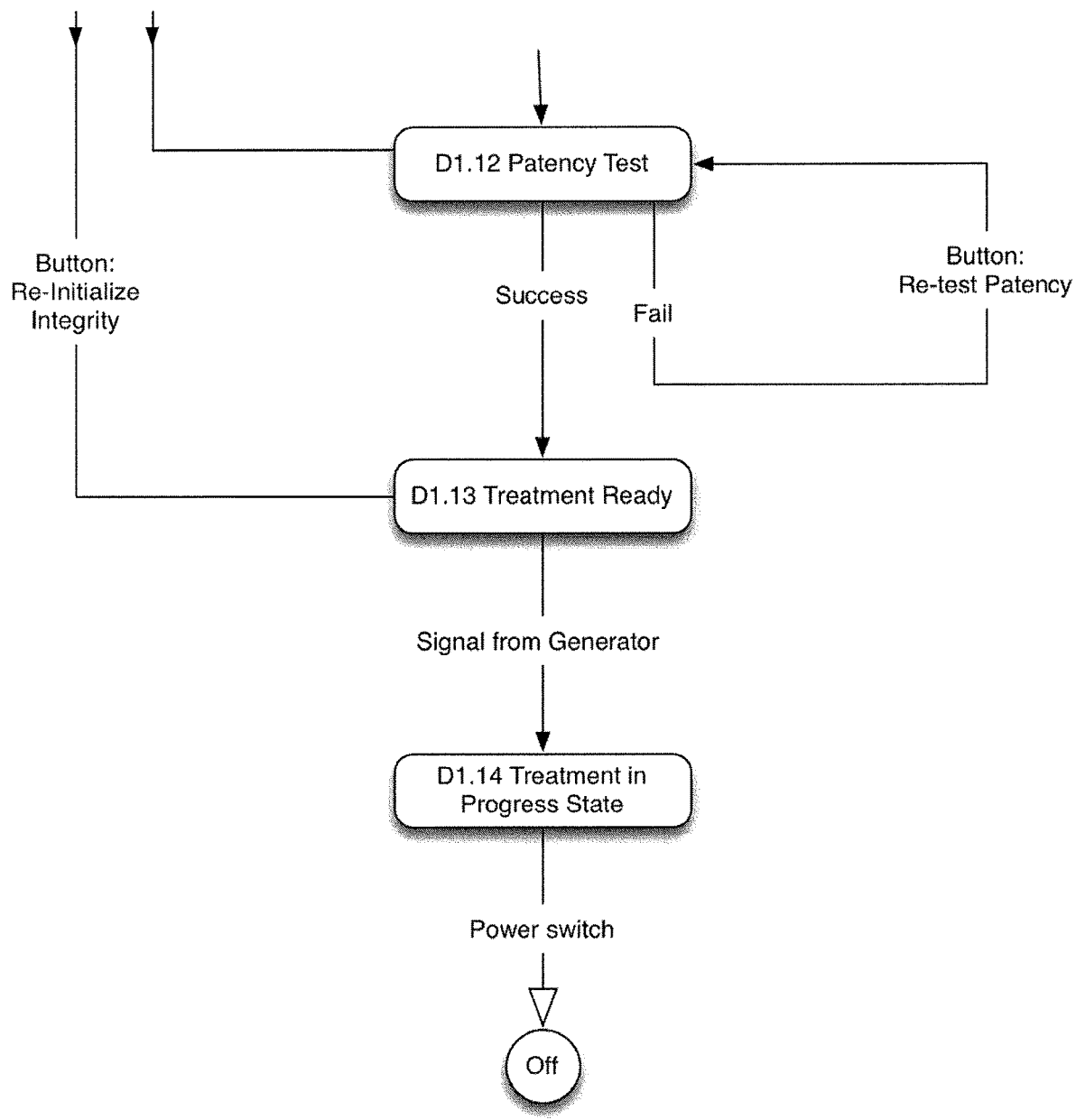

FIGS. 7A-7B describe an example of an algorithm for utilizing uterine integrity and patency tests for a uterine ablation procedure. First, a uterine device, as described above, can be inserted into the uterus of a patient. In some embodiments, saline can flow through a flow meter and both the inflow and outflow lumens of the uterine ablation device during insertion into the patient. Once the device has been placed in the uterine cavity, the cervix can be sealed by one or more balloons, such as the distal, central, and proximal balloon described above. Upon sealing the cervix, an integrity test can be initiated. As described above, a flow of gas/fluid from the uterine ablation device can be measured with a flow meter, and the system can monitor for a flow rate through the flow sensor to decrease to a flow rate threshold. Once the flow rate threshold is reached, (e.g., 5 ml/min in one embodiment), it can be determined that the uterus is sealed and the system can then begin the patency test. The patency test maintains flow into the uterine cavity with the inflow lumen of the device, but opens the outflow lumen to remove gas/fluid from the uterine cavity into a waste container. The flow rate threshold is then monitored during patency test. A flow rate above a patency test threshold (e.g., greater than 5 ml/min in one embodiment) can indicate that the lumens are not clogged or that the distal end of the uterine ablation device is not embedded into tissue. If the patency test threshold is not satisfied, the physician should repeat the insertion steps and repeat the integrity test and patency test prior to initiating uterine ablation. If the patency test threshold is satisfied, the uterine ablation treatment can begin as indicated in FIGS. 7A-7B.

In some additional embodiments, the return channel for the integrity test may or may not be the same return line used in the therapeutic mode to evacuate vapor and bodily fluids/tissue from the uterus. More specifically, in some embodiments the device may have its own dedicated return channel system specifically for carrying out the integrity test. In another embodiment, the return channel may have its own active or passive outflow regulator. In yet another embodiment, the return channel could have a second flow meter (not shown) that can be used to compare flow coming into the uterine cavity (via flow meter 126) versus the flow monitored on the egress from the uterine cavity (via the second flow meter within the return channel). Comparing the flow-out versus the flow-in can provide a dynamic measurement for the presence of leaks in the uterus or a lack of integrity.

In an additional embodiment, a system can be employed combining both a solenoid valve and a second flow meter in the return channel. In this embodiment, a series of return channel closures by the solenoid valve in combination with the measurement of flow during open cycles can provide indications of uterine cavity integrity and the amount of volume in that space. In some embodiments a recording and data analysis system can be incorporated to analyze the flow rate measurements and provide automation of actions based on the integrity of the uterus and position of the ablation device. This analysis system records the flow rate at various stages of the treatment and provides appropriate feedback to the user and ablation device.

Figure 5:
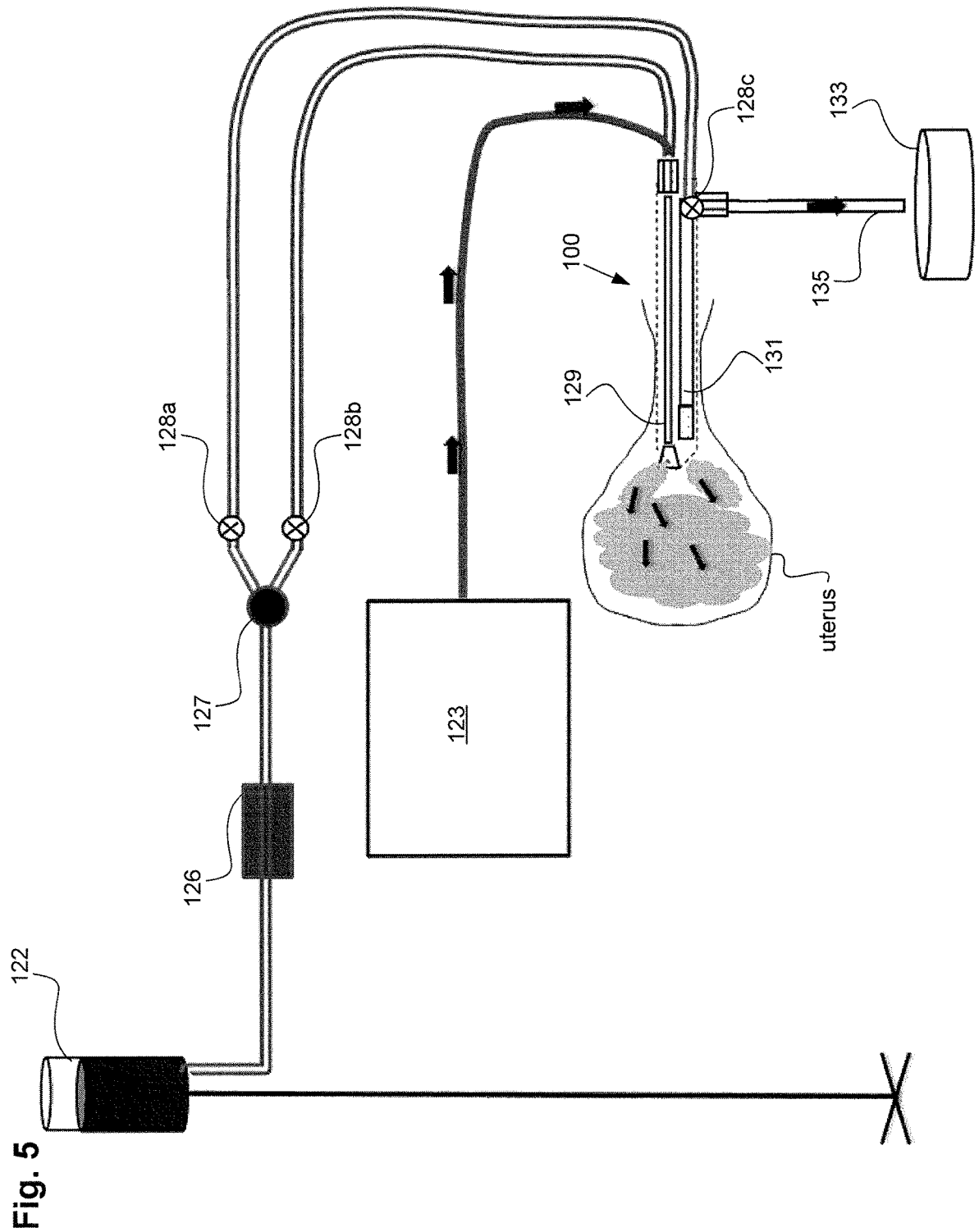
FIG. 5 illustrates one configuration of a uterine ablation device during a vapor treatment operation.

Once the device has been properly positioned and the integrity test and patency tests determine that the uterus is sealed, the device is properly placed and an open communication between the delivery and return lumen exists, a heated condensable vapor can be delivered from the distal tip 106 of ablation device 100 through vapor ports 107 (of FIGS. 1A-1B) to the uterus to ablate the uterine tissue. FIG. 5 illustrates another view of the ablation device delivering vapor to the uterus. In one embodiment, vapor can be delivered to the ablation device via vapor source 123. In another embodiment, not shown, the gas/fluid source 122 can be used to provide a fluid, such as saline, to the device where it can then be converted into vapor to deliver to the uterus. Once the vapor has been delivered to the uterus through inflow lumen 129, the vapor can be removed from the uterus through outflow lumen 131 and deposited in waste container 133 via tubing 135.

Maintaining uterine distension or pressure within the uterine cavity during integrity and patency tests, and immediately prior to the initiation of vapor treatment without deflation May or may not be performed. In some embodiments, a distended uterine cavity under a pressure below 70 mmHg without deflation will experience less blood and debris accumulation within the inflow and outflow lumens of the uterine ablation device prior to treatment. Reducing the accumulation of blood and debris in the return or outflow lumens will reduce procedure time and improve treatment efficiency. Reducing the accumulation of blood and debris in the return or outflow lumen can occur for a time duration encompassing the insertion of the device into the uterine cavity to the initiation of ablation treatment, which in cases can be 1 to 5 minutes. Greater time durations benefit further from the reducing the accumulation of blood and debris.

The initiation of vapor treatment can begin immediately following the completion of the integrity and patency tests. In some embodiments, this action can be controlled by software within the main generator unit. Alternatively, the integrity and patency tests can be conducted by a unit or module separate from the main generator that provides an indication that the treatment procedure is ready to begin utilizing the algorithm illustrated in FIG. 7. The opening and closing of various lumens during the integrity and patency tests can be performed by solenoid valves or balloons that pinch off the lumens.

In one embodiment, utilizing saline over gas as the media for performing the integrity and patency tests has the following advantages. It has been empirically determined that the application of heated vapor may not traverse an intentionally placed perforation in a uterine cavity whereas the same intentionally placed perforation can be traversed by saline media during an integrity test. In addition, in a uterine cavity of a living patient in test conditions, active bleeding can occlude or impede the ability of gas to traverse an intentionally created perforation, thereby providing a false indication of uterine integrity to the physician. For example, the perforating instrument can be a cervical dilator of 3 mm in diameter and the angle of perforation can be 15 degrees to normal, or perpendicular, to the uterine surface. Smaller and larger diameter instruments can be utilized.

Saline is also readily available in clinical use. In practice, gas such as carbon dioxide is administered to a patient within a safety threshold flow rate typically below 100 ml/min and at this rate, the gas may be ineffective in removing blood or other debris in the uterine cavity that may occlude or impede the interpretation of a potential perforation.

Also, in clinical use, incorporating saline over gas as the media for the integrity and patency tests provides a rinsing source for the lumens in vivo. This rinsing or diluting action can facilitate the open communication between the input and output lumens of the uterine ablation device prior to vapor treatment. The use of saline is particularly suited for diluting blood which may accumulate within the lumens of the uterine device.

Figure 6A:
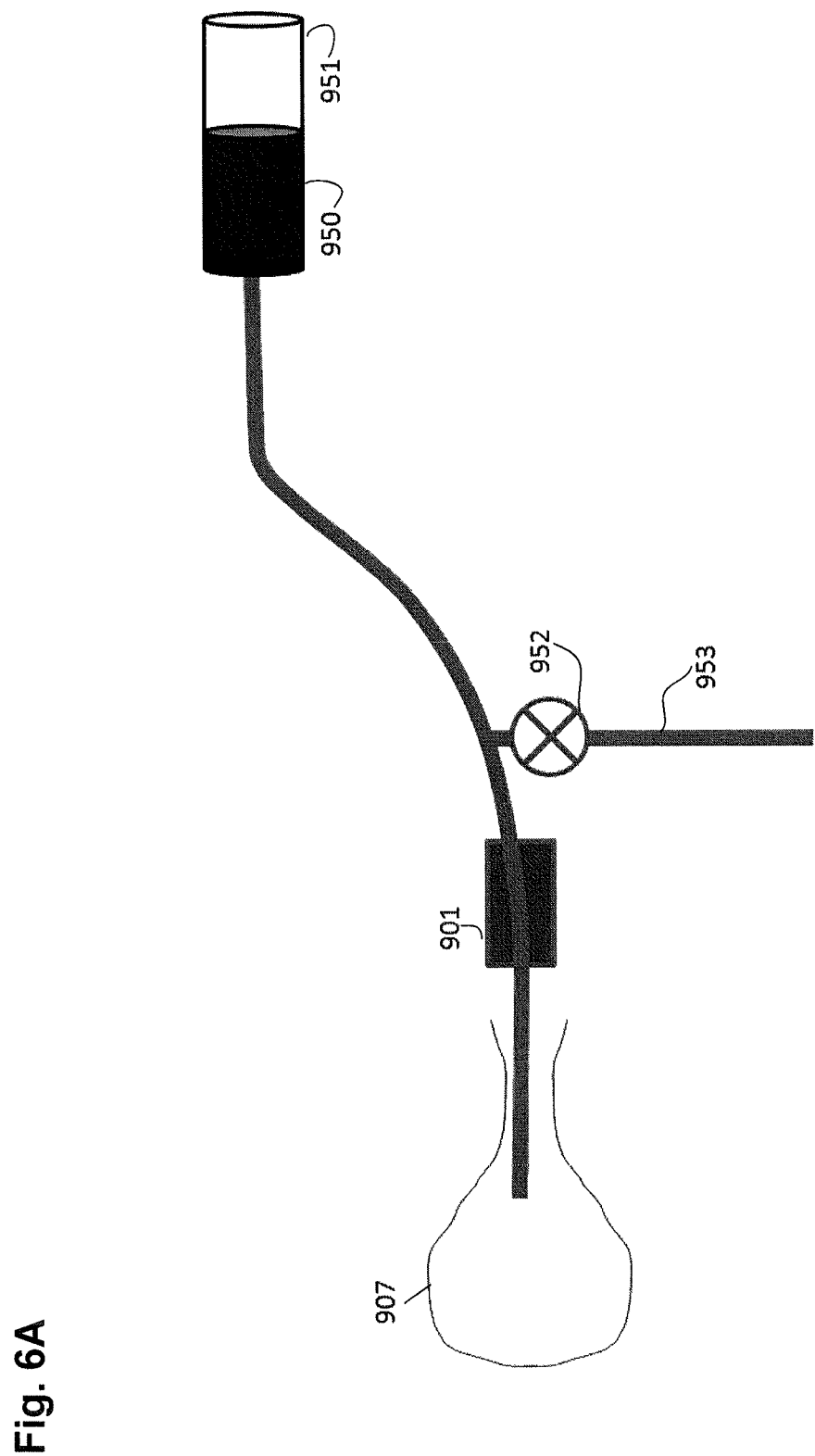
FIG. 6A illustrates one configuration of an apparatus during a uterine integrity test.

Alternatively, an entirely flow-driven system may be used to perform the integrity and patency tests. In the flow driven system, as seen in FIG. 6A, a fluid 950 may be delivered distally towards the device and uterus. The fluid 950 may be saline, for example. The fluid 950 may be housed in a container 951. The container 951 may drive the fluid at a known or a variable rate. For example, in one embodiment the container 951 may be a syringe or peristaltic pump. The fluid 950 may be a gas and the container 951 may contain a propeller to propel the fluid. A valve 952 with a set crack pressure may be positioned proximal to a flow sensor 901. The valve 952 may have a crack pressure set at 60-70 mmHg, for example. Before the pressure in the uterus reaches the crack pressure of the valve 952, the flow sensor 901 may see a non-zero flow value. Once the pressure inside of the uterus 907 equals the crack pressure of the valve 952, the fluid 950 will cease flowing into the uterus 907 and may instead flow into a lumen 953. The lumen 953 may exit into atmosphere and provide no back pressure. A continued non-zero flow value may indicate a non-sealed uterus. The flow sensor may instead be positioned on line 953 if the flow value at the container 951 is known or measured. Positioning the flow sensor on line 953 may be advantageous to keep the flow sensor 953 out of the sterile field. The flow-driven system described herein may be performed without monitoring or measuring pressure within the uterine cavity.

Figure 6B:
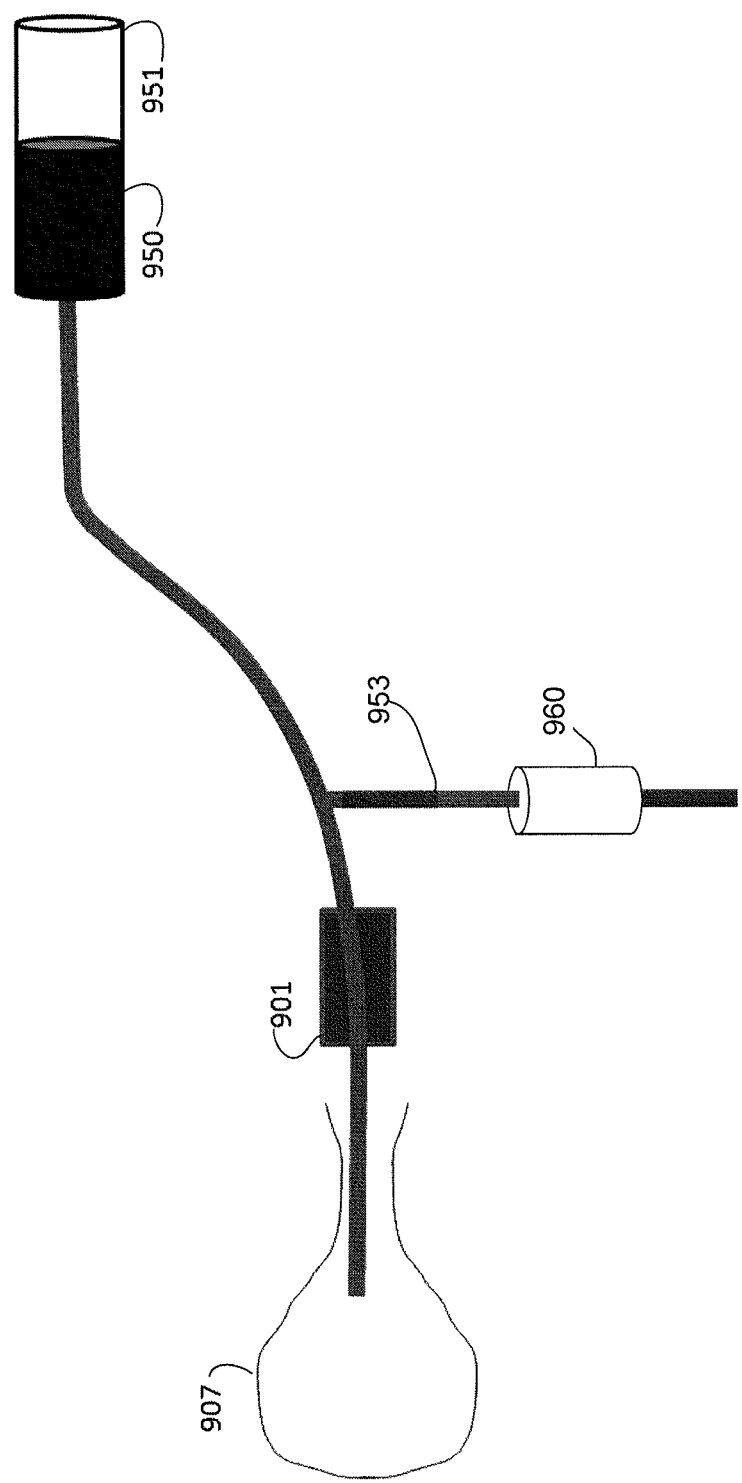
FIG. 6B illustrates another configuration of an apparatus during a uterine integrity test.

As another embodiment, a system for performing an integrity test can be independent of pressure and as an example, remove the requirement for setting the height of a saline source to a know level. In addition, some embodiments can remove the requirement for placing a pressure relief valve within the system with a known cracking pressure. To illustrate this embodiment, as seen in FIG. 6B, a delivery flow of the fluid 950 is known and can be set to a constant value, for example by a pump 951, then an orifice 960 with a known resistance to the fluid may be placed in-between the fluid source and the uterus 907. Orifice 960 can be any component with a known orifice or bore size, such as, for example, a hypodermic needle with a known caliber and inner diameter. The orifice 960 may be positioned at a known height relative to the uterus 907. For example, the orifice 960 may be placed in the handle of the intrauterine device. The orifice 960 may be tuned with the flow of the fluid to yield a predictable pressure in the uterus 907. For example, if the fluid 950 is flowing at 10 mL/min and the orifice has an inner diameter of 0.01 inches and a length of 0.5 inches, then the intrauterine pressure may never exceed a threshold value, such as 60 mmHg. For example, when the pressure in the uterus is zero (gauge), then the majority of the fluid 950 may flow into the uterus 907. As the uterus 907 is filled with the fluid 950, the pressure in the uterus 907 may increase and the excess fluid 950 may instead flow through the orifice 960. Eventually, all of the fluid 950 may flow through the orifice 960. A flow sensor 901 may be placed as shown in FIG. 6B or may be placed on lumen 953 so as to measure flow through the orifice, for example. The lumen 953 and/or the flow sensor 901 may be completely and/or partially outside of the sterile field. An integrity test may be performed by monitoring the flow of the fluid 950 using the flow sensor 901. For example, if all of the fluid 950 is being diverted through the orifice 960, then the uterus may be considered fully sealed.

Figure 8:
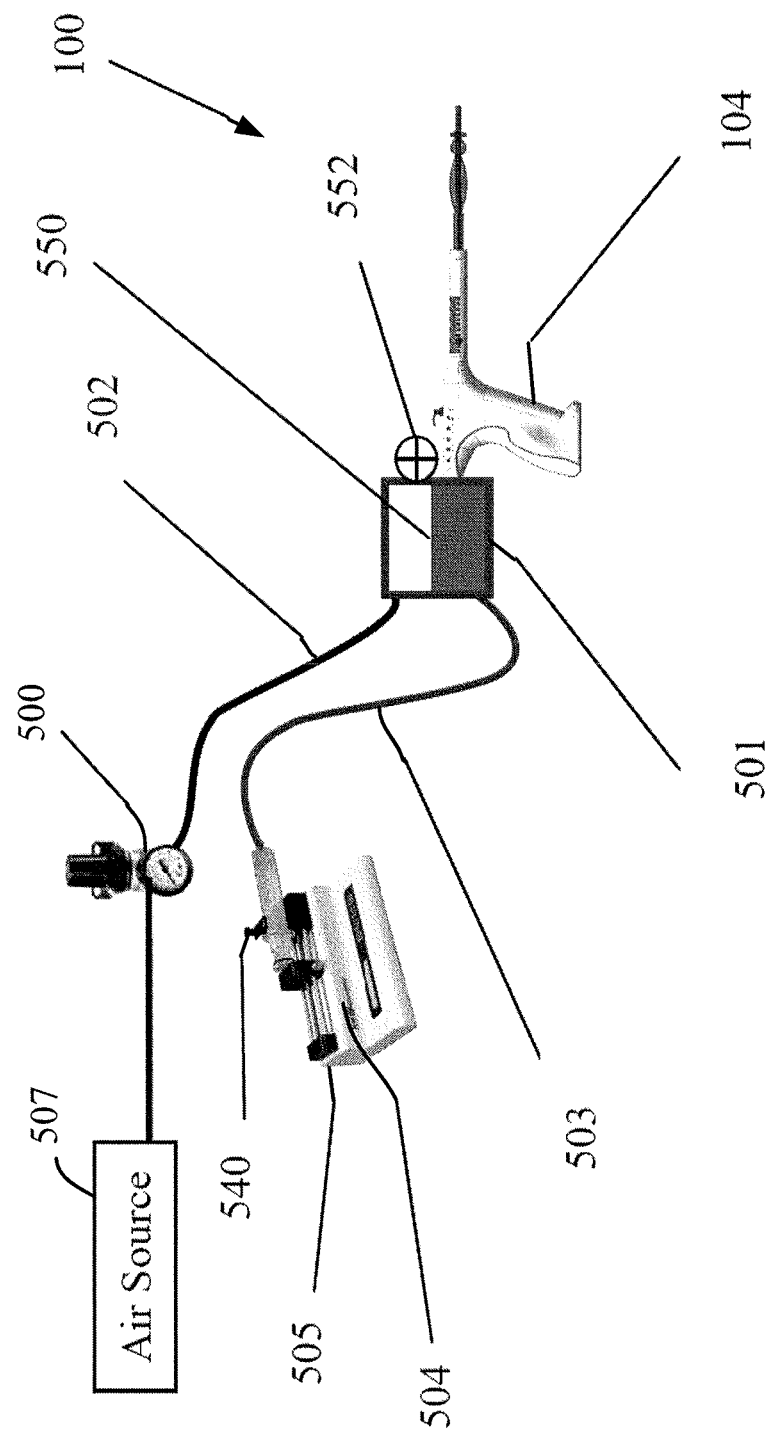
FIG. 8 illustrates a system that removes the requirement for a specific height requirement for the irrigation source during an integrity and patency test.

FIG. 8 shows one embodiment of a uterine ablation device, which can include some or substantially all of the components of the uterine ablation device of FIGS. 1A-1B. In FIG. 8, the uterine ablation device 100 includes a fluid reservoir 501 that is pressurized by an air or pressure source 507 connected to and controlled by an air pressure regulator 500 via conduit 502. The air or pressure source 507 can comprise, for example, a pressurized gas or air tank. In other embodiments, the air or pressure source could instead be a constant force spring or other element with a known constant force to provide a pressurized source of air. In one specific embodiment, an elastic, resilient piece of tubing such as a thin walled latex, PVC balloon, or other compliant balloon could also take the place of the spring and or pressurized air source by expanding while distended with air and utilizing the resultant pressure in the balloon to supply the pressurized air source.

In one embodiment, fluid reservoir 501 can be located within a handle 104 of a uterine insertion device 100 that is configured for delivering vapor to the uterine cavity. This configuration is particularly suited for handle 104 delivering vapor independent of the patient's uterus (not shown) height relative to the fluid reservoir 501. The described system does not require a patient uterus height measurement relative to the fluid reservoir 501 of the uterine ablation device 100 prior to performing the integrity test.

The air pressure regulator 500 can be used to set the fluid or liquid pressure within the fluid reservoir 501 via conduit 502. The fluid level 550 at the air-fluid interface in the fluid reservoir 501 is monitored by one or more sensors 552. The sensor(s) 552 can comprise, for example, an optical sensor, a flow sensor, an infrared sensor, a contact sensor, a magnetic sensor, an ion sensor, or similar sensors that respond to detection of a fluid level. The monitored fluid level 550 is communicated to the controller of the device in a feedback loop to maintain the fluid level at the appropriate level.

When the fluid level 550 in the fluid reservoir 501 falls below a lower threshold as indicated by sensor(s) 552, the fluid supply system 504 is controlled by the controller to inject more fluid into the reservoir until the upper threshold of the fluid level 550 is reached.

The fluid supply system 504 contains a syringe 505 and a stepper motor or pump 540 to deliver the fluid. In some embodiments, the fluid supply system 504 and measures the flow rate of fluid as it supplies fluid via conduit 503 into the fluid reservoir 501. The flow rate can be measured with a sensor, or alternatively, the flow rate can be determined based on the operation (cycle speed) of the syringe pump. In another embodiment, sensor(s) 552 can be used to estimate the flow rate by monitoring the amount of time it takes for the fluid level to reach the upper threshold after falling below the lower threshold. The fluid supply system can include fluids such as saline, water, distilled water, or the like.

A method of using the embodiment of FIG. 8, includes the steps of:

1) Opening the fluid reservoir 501 to atmosphere (for example, the air pressure source 507 and air pressure regulator 500 are not connected and/or are not pressurized via conduit 502.)

2) Operating the fluid supply system 504 until the fluid level 550 reaches an upper threshold in the fluid reservoir 501. In practice this sensor 552 could be infrared, tactile, contact, magnetic, ion, or similar sensors that respond to the detection of a fluid level.

3) Close the fluid reservoir 501 to atmosphere.

4) Pressurize the pressure source with the air pressure regulator 500 to pressurize the fluid reservoir 501 to a preferred range of 52 mmHg to 60 mmHg, urging the fluid in the fluid reservoir 501 to exit through the handle 104 of the uterine ablation device 100. Other ranges of pressure for the fluid reservoir 501 are possible depending upon the clinical application and the bodily cavity being inspected for integrity.

5) If the fluid falls below a lower threshold (e.g., below the range sensed by a sensor 552), then the syringe can be advanced until the fluid level rises above an upper threshold (which may be the same and/or different than the lower threshold). Algorithms are used by the controller to detect a leak in response to the measuring the actions of the syringe: For example, if the fluid does not fall beneath the lower threshold for >15 seconds, or if the average syringe flow <5 mL/min for 15 seconds (e.g., counting steps, monitoring current/voltage, etc.)

6) If the system does not pass the integrity test within a predetermined time period (e.g., 60 seconds), then the uterine ablation device notifies the user that the integrity test is failed. Pull device out and check condition of device and also check to see if there are any conditions in the patient.

In an alternative embodiment, the uterine ablation device 100 above works with the same steps except the fluid reservoir 501 does not need to open and is closed to atmosphere and thereby does not need to conduct steps 1 and 3.

If a leak occurs within the uterine cavity or system, the fluid supply system will continue to operate to fill the fluid reservoir to the threshold level. Once the threshold or predetermined level is reached, the stepper motor or pump will stop advancing. The determination of flow rate can be performed by assessing the operation of the syringe or the stepper motor/pump. Experiments using the system described above in a simulated silicone uterus model demonstrated high accuracy and sensitivity in terms of leak detection.

Figure 9:
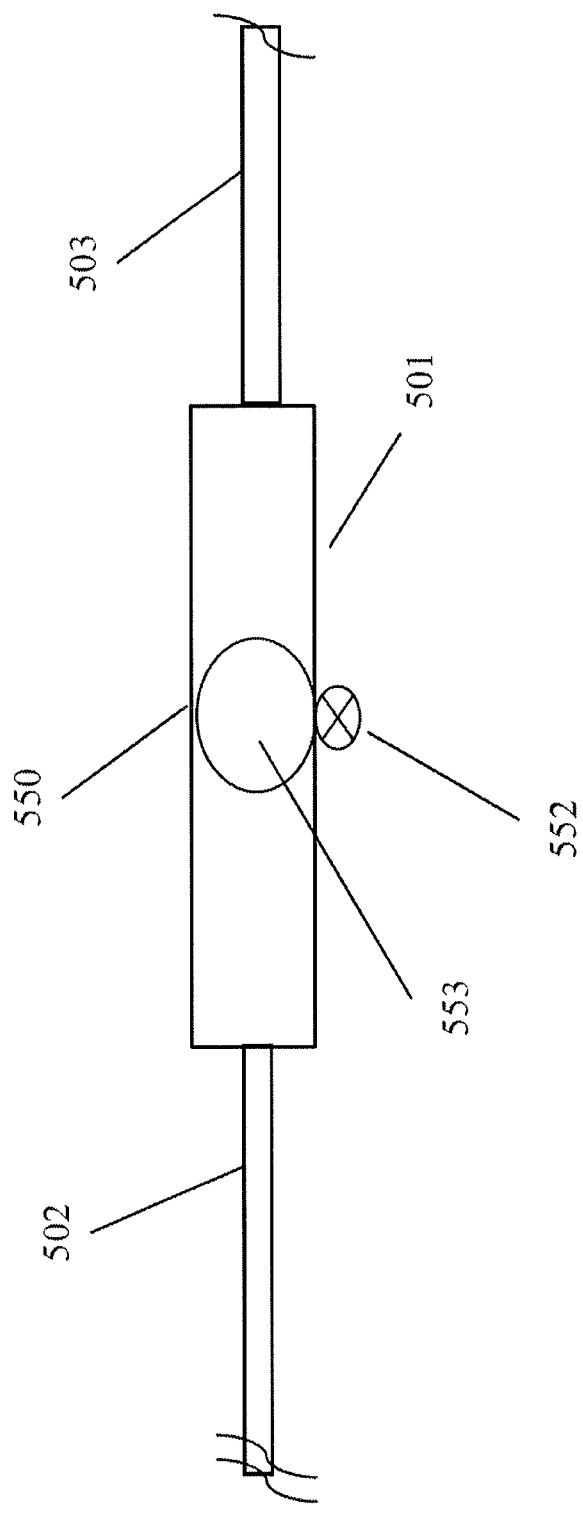
FIG. 9 illustrates an embodiment that utilizes a ball or bladder to facilitate detection in the air-liquid interface.

FIG. 9 illustrates another embodiment that improves the sensitivity of sensing fluid level 550 within fluid reservoir 501 with sensor(s) 552. In this embodiment, an air-filled bladder 553 may be placed between the liquid and the air in the fluid reservoir 501. Pressurized air is supplied to small reservoir 501 as described above via air conduit 502, and reaches up to the air-filled bladder 553. The position of the air-filled bladder 553 in the fluid reservoir 501 defines the fluid level 550. Opposite the air conduit 502, a fluid conduit 503 supplies fluid to the fluid reservoir 501 as also described above.

In practice, the air-filled bladder 553 resides at fluid level 550 and provides greater detection by sensor(s) 552 of changes in the fluid-air interface. Air-filled bladder 553 alternatively can be constructed as a ball from a solid plastic that has buoyancy, or metallic materials for improved detection, or an internal RF emitter for an alternate mechanism for detection. Enhancing fluid level 550 with air-filled bladder 553 provides the following benefits:

1) Less mixing of air and liquid at fluid level 550 reduces chance of air entering the uterus.

2) Possibly improved sterility since the air supply that contacts the fluid would not require a filter or sterile air barrier. An example of a sterile air barrier is a 0.2 micron filter.

3) Less dependency on orientation since the small reservoir 501 can be tilted sideways, upside down, or generally in movement if contained within the handle of the uterine ablation device (not shown) without getting air into the uterus.

4) Air-filled bladder will make fluid level 550 easier to detect as opposed to a level that can undergo changes as the small reservoir 501 and liquid experiences movement.

5) Reduced risk of liquid going into the air line. The air-filled bladder 553 can prevents retrograde fluid travel into the air conduit 502 as the air-filled bladder 553 creates a seal in the small reservoir. The seal in the small reservoir can be enhanced by a tapered or reduced internal diameter in small reservoir 501 closer to air conduit 502 to prevent further advancement of liquid in the small reservoir 501.

Although FIG. 9 shows fluid reservoir 501 and corresponding fluid level 550 in a horizontal position or alignment, the air-fluid interface can be upright or vertical, horizontal, or angled since the fluid level 552 is agnostic to alignment of the small reservoir 501. In addition, the placement of a one-way valve distal to the fluid reservoir 501 can advantageously reduce or eliminate the effect of uterine contractions on the fluid level 550 within the fluid reservoir 501.

Figure 10:
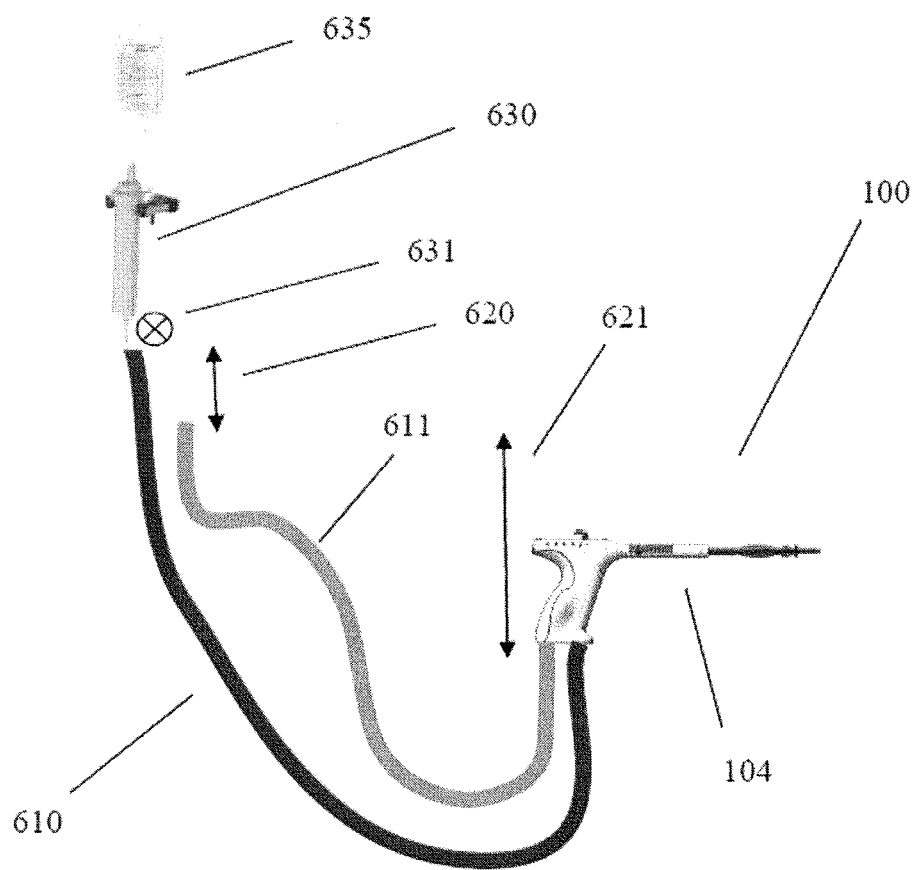
FIG. 10 illustrates a system that utilizes a manometer that determines the height of the endometrial ablation device in relation to the patient.

FIG. 10 illustrates another embodiment of a uterine ablation device 100 that utilizes a manometer defined by fluid conduits 610 and 611 to determine the height 621 of the handle 104 of the uterine ablation device 100 relative to the height 620 of a pressurized fluid source 635. The pressurized fluid source can comprise, for example, a saline bag or a separate fluid column 620. The manometer may measure either pressure or the height 620 of the pressurized fluid source 635.

In practice, the pressurized fluid source is raised, based on the manometer results, such that the height of the pressurized fluid source 635 is ~32 in above the height of the uterus or handle 104. A drip chamber 630 having a predetermined flow rate or drop size (e.g., 10 drops/mL) is located in series to fluid conduit 610 and pressurized fluid source 635. A drop counter 631 (e.g., infrared beam sensor, infrared sensor, acoustic sensor, or the like) can be placed at the drip chamber 630 to monitor the flow of water during the integrity test. In one embodiment, the integrity test can be passed if flow through the drip chamber <5 mL/min for >15 sec).

FIG. 11 illustrates another embodiment of a uterine ablation device, including a relief valve 701 within the handle 104 configured to eliminate the need for measuring the height of the handle 104 relative to the fluid source prior to performing an integrity test. A fluid supply system 504 including syringe 505 and stepper motor or pump 540 is configured to supply fluid as described above. The flow rate measurement of the fluid going through fluid conduit 503 and into handle 104 can be determined by counting the steps of the stepper motor or cycles of the pump.

The relief valve 701 is configured to open at a factory-set pressure (e.g., 60 mmHg). The fluid supply system 504 drives fluid into the uterus at a specified flow rate until the relief valve 701 opens to relieve excess pressure from the uterine cavity. In practice the described system can operate with the following principles:

1) The stepper motor or pump 540 operates at a speed whereby the relief valve 701 initiates opening or displacement of the internal diaphragm or plug and the step counts are used to estimate flow rate; or 2) The fluid supply system 504 delivers fluid at a "passing" flow rate (e.g., <5 mmHg) and fluid must be observed flowing out of the relief valve 701. A passing integrity test is indicated by a reduction in flow rate from the stepper motor or pump 540 below a predetermined threshold.

Figure 12A:
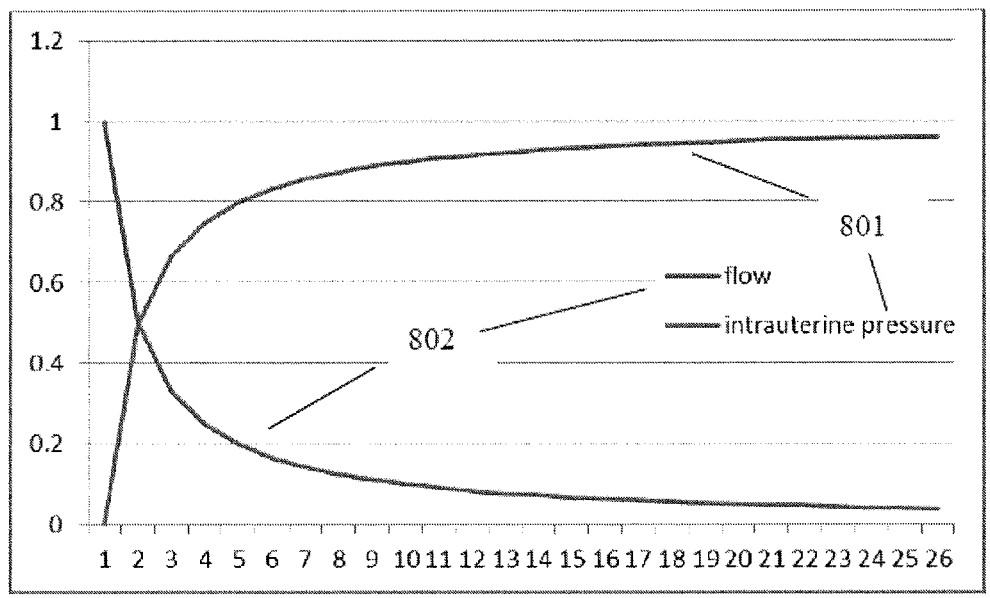
FIG. 12A-B illustrate graphs of flow versus intrauterine pressure.

FIG. 12A illustrates a graph of a gravity-fed system supplied by a raised saline bag that is at a height greater than the device that is measuring the pressure within the uterus. On the fluid source, the rate of fluid going into the uterus is monitored. The graph demonstrates the relationship of intrauterine pressure 801 versus flow rate 802. For an intact uterine cavity and increasing intrauterine pressure 801, the corresponding flow rate 802 steadily decreases. The upper end of intrauterine pressure 801 reaches a plateau defined by the height of the saline bag.

Figure 12B:
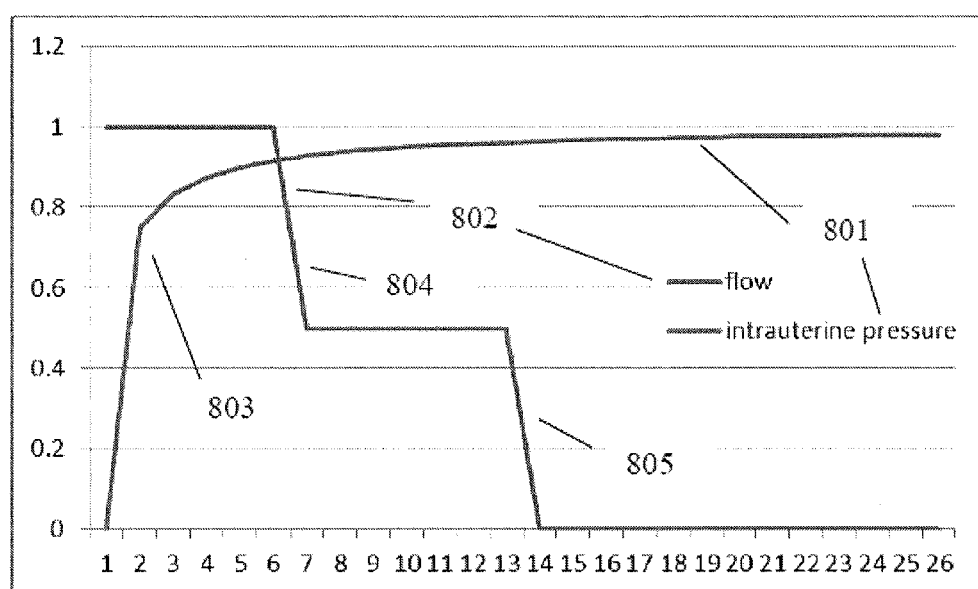

FIG. 12B illustrates a graph of an improved control of pressure or flow in real-time. The curves demonstrate that controlling fluid flow rate 802, as an example, a steady control of flow rate 802 can more quickly increase the intrauterine pressure 801 in section 803 to reduce the amount of time to perform the integrity test. In addition, steep drops in flow rate 801 can be used to further interrogate uterine integrity and intrauterine pressure 801 as seen in sections 804 and 805.

Figure 13:
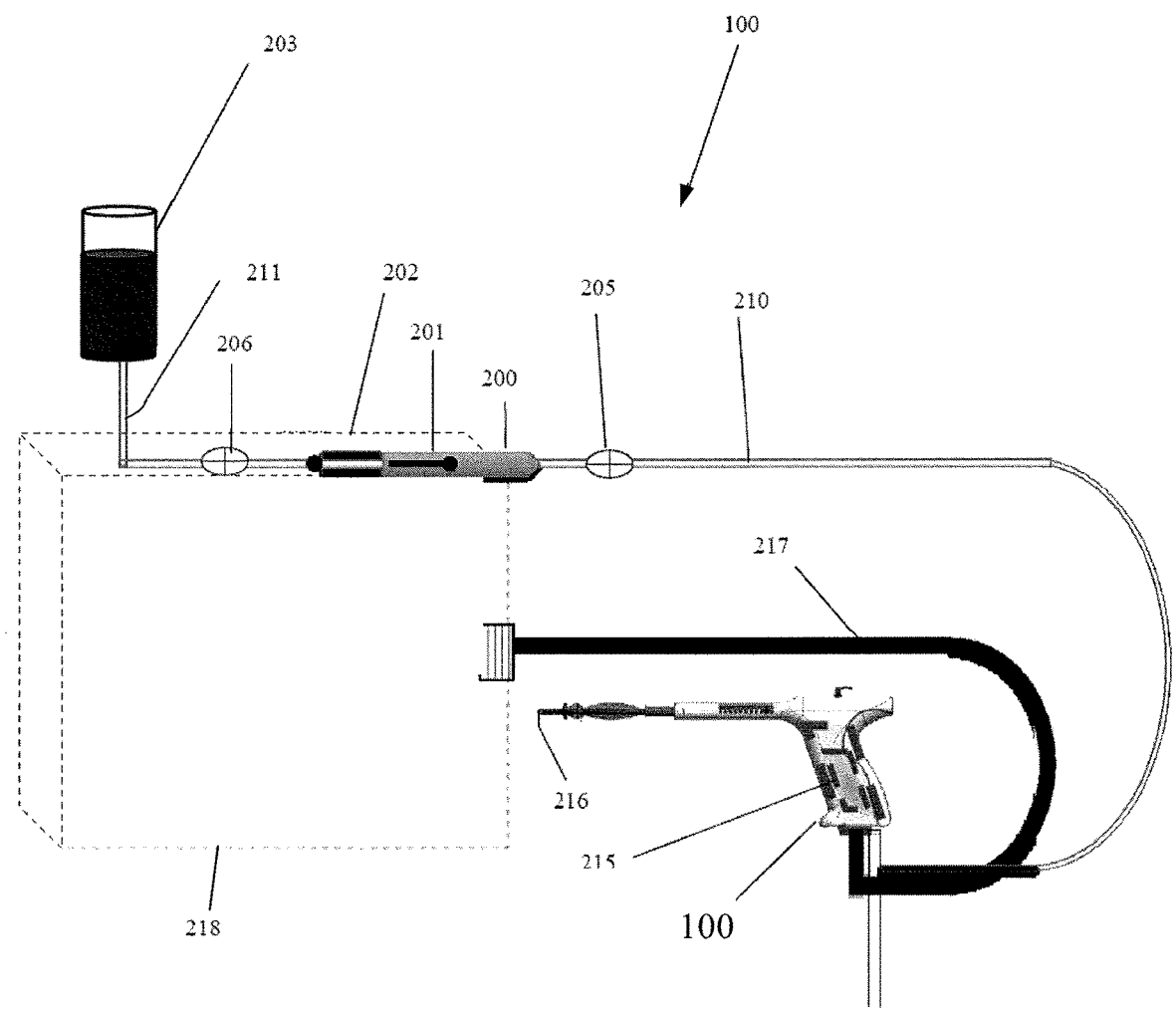
FIG. 13 illustrates a system with a refillable syringe delivering fluid through a vapor probe for performing the integrity and patency test, and for providing the fluid to create vapor.

FIG. 13 illustrates another embodiment of a uterine ablation system including a syringe 200 that can be used to deliver fluid through a uterine ablation device 100. The fluid can be used for performing the uterine cavity integrity test, the patency test, and for creating vapor for thermal ablation. As described above, fluid may be supplied by syringe 200 by the displacement of syringe plunger 201 caused by stepper motor or pump 202. Fluid enters the uterine ablation device 100 via conduit 210 from the syringe 200.

In one embodiment, heating coil 215 is disposed in the uterine ablate device and heats the fluid to create vapor that can be delivered through the distal outlet 216 of the device. Heating coil 215 can be energized, monitored, and controlled by generator 218 via conduit 217.

In practice, syringe 200 may need to supply a fluid volume from a fluid source 203 that has a larger volume of fluid than the syringe 200 being used. There is also often a need to minimize delays in supplying the fluid by the syringe 200. To achieve accurate delivery, a stepper motor or pump 202 may be used to control the position of syringe plunger 201 in syringe 200. In one embodiment, a one-way valve distal 205 distal to the syringe 200 allows the syringe 200 to be refilled from supply container 203 without disconnecting the syringe from the uterine ablation device. In addition, a one-way valve 206 between the syringe 200 and the supply container 203 prevents the backflow of fluid to the supply container 203 while permitting the flow of fluid from the supply container 203 to the syringe 200. In operation, one-way valve 206 is activated in the syringe re-filling step that can be actuated manually by the end user or automatically by the generator (not shown) controlling the uterine ablation device 100.

Alternatively, as opposed to the one syringe 200 described above, two syringes could be used in parallel, so that when the first syringe is emptied, the second syringe can immediately begin delivering fluid. Simultaneously, the first syringe can be in the state of being refilled by a fluid supply source. For the two syringe configuration, two separate conveying mechanisms on the corresponding syringe plungers would be required to control the plunger movement of each syringe. In another embodiment, the two syringes can be positioned facing in opposite directions, and one syringe could fill as the other empties. With this configuration, only one conveying mechanism would be required although the syringe plungers would need to be connected to each other and to the conveying mechanism.

Alternatively, the syringe 200 can include a plurality of chambers, so that while the syringe is delivering fluid from one chamber, another chamber could be simultaneously refilled with fluid from the supply container. This would result in minimal time lag for the fluid being delivered through the uterine ablation device. In this embodiment, one common conveying mechanism such as stepper motor or pump achieves simultaneous delivery from one chamber while the other is being refilled. The multi-chamber syringe could have two or more ports per chamber: one for refilling and one for delivering fluid. A one-way valve could be placed on each port to control flow as described in the first above. The valves could be actively and/or passively controlled. For example, the valves could be controlled with mechanical motion, electrically, and/or via pressure differentials. One chamber of the double-acting syringe may be easier to purge of air bubbles than another end. Certain operations may be more sensitive to bubbles in the fluid pathway than others. Thus, for some operations, both chambers could be used (e.g., during device insertion into the patient) whereas for other operations only the purged side could be used (e.g., during vapor delivery).

In addition, there is also the need to deliver fluids with a required accuracy that can be affected by overall volume capacity of the syringe delivering the fluid, and the accuracy of syringe plunger displacement. To improve the measurement of plunger displacement, the pressure being applied to the syringe (e.g., by the stepper motor or the pump) may be monitored. For example, a pressure transducer could be in contact with the fluid in the syringe, or a strain gauge could be placed on the syringe (or other fluid-contact components). The force used to drive the syringe could be used to predict the internal pressure.

Figure 14:
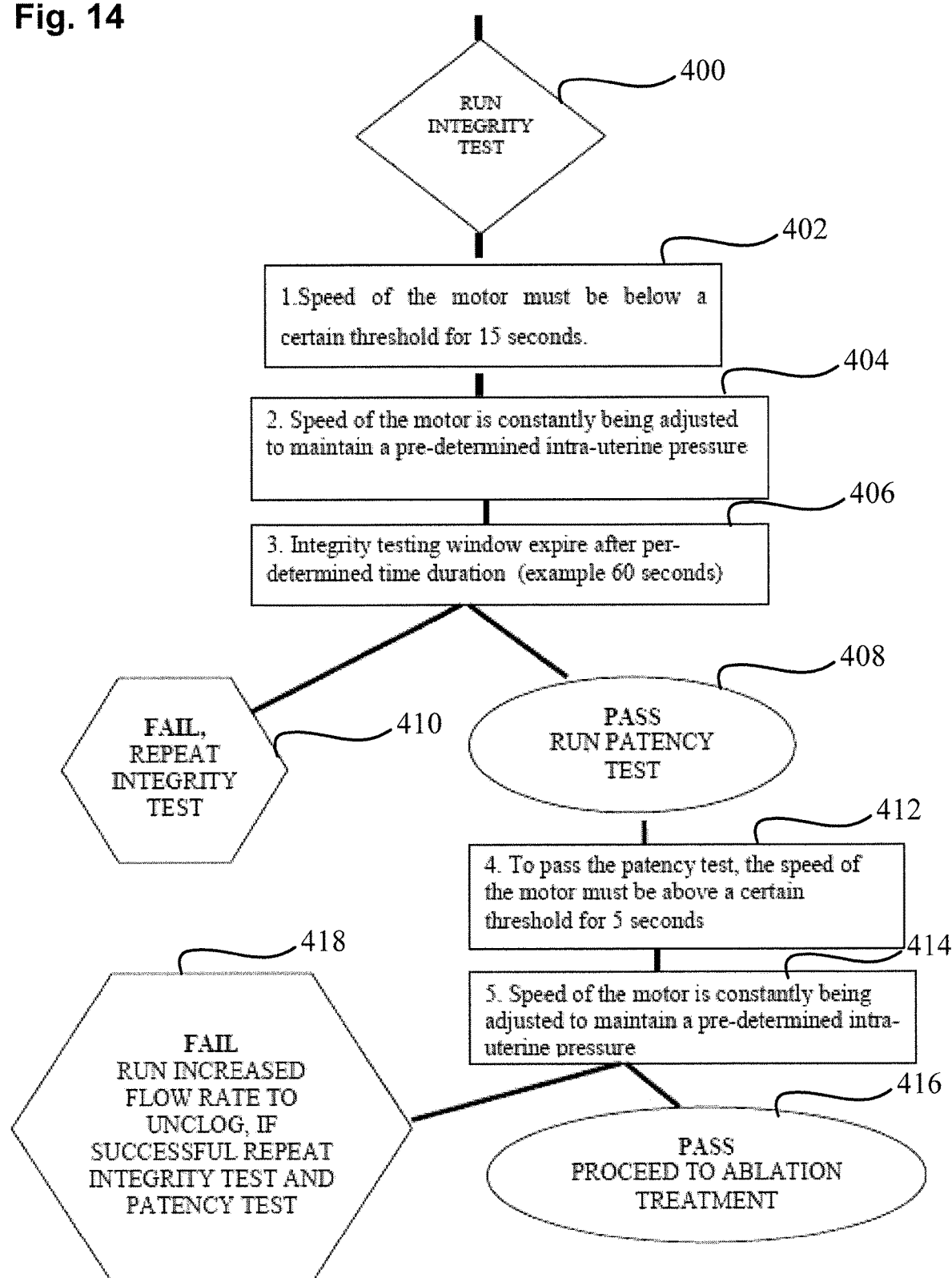
FIG. 14 illustrates a process for improving the patency test by increasing the fluid flow rate when a failed patency test is encountered.

FIG. 14 shows a flow chart describing the method steps performed by a uterine ablation device described herein to perform both integrity and patency tests: At step 400 of FIG. 14, the integrity test is initiated. To pass the integrity test, the speed of the motor must be below a certain threshold for a predetermined time period (e.g., 15 seconds), as shown in step 402. The speed of the motor is constantly being adjusted during the integrity test (step 404) to maintain a predetermined intra-uterine pressure (e.g., RPM=(55 mmHg−intra-uterine pressure)*constant. The integrity testing window expires after a predetermined time period (e.g., 60 seconds), although the operator could repeat the test as necessary, as shown in step 406.

If the integrity test is passed at step 402, then the patency test is initiated at step 408. If the integrity test is failed, then steps 402, 404, and 406 are repeated.

To pass the patency test, the speed of the motor must be above a certain threshold for 5 seconds as shown in step 412. The speed of the motor is constantly being adjusted to maintain a predetermined intra-uterine pressure (e.g., RPM= (55 mmHg−intrauterine pressure)*constant), as shown in step 414. If the patency test is passed, then ablation is initiated at step 416. If the patency step is failed, then the system can attempt to unclog the device by running an increased flow rate through the device to attempt to unclog the device. Then steps 412 and 414 can be repeated.

The integrity test described above can be performed with feedback loops to keep the uterus at the target pressure with an intrauterine pressure monitor using pressure sensor. Alternatively, the intrauterine pressure sensor can be used to determine desired Drive Flow defined as:

Drive Flow (mL/min)=(55 mmHg−intrauterine pressure measurement)*2;

If intrauterine pressure is 55 mmHg, then the syringe stops flowing.

In addition, the system can convert the desired Drive Flow to step speed for stepper motor. For example, 1 mL/min=500 steps/second.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method of performing an integrity test for a uterus of a patient, comprising the steps of:
    inserting a uterine ablation device into the uterus of the patient;
    activating a fluid supply system to deliver fluid into a reservoir disposed on or in the uterine ablation device;
    deactivating the fluid supply system when a level of an air-fluid interface within the reservoir reaches an upper threshold;
    pressurizing the fluid in the reservoir with a pressure source acting through a pressure regulator to deliver the fluid from the reservoir of the uterine ablation device into the uterus;
    measuring the level of the air-fluid interface within the reservoir with one or more sensors of the reservoir;
    re-activating the fluid supply system when the level of the air-fluid interface within the reservoir reaches a lower threshold; and
    determining that there is a leak in the uterus when a flow rate of the fluid supply system does not remain below a flow rate threshold for a predetermined amount of time over the course of an integrity testing time period.

2. The method of claim 1, wherein the reservoir is opened to atmosphere prior to the activating step.

3. The method of claim 1, wherein the reservoir is closed to atmosphere after the deactivating step.

4. The method of claim 1, further comprising determining that there is not any leak in the uterus when the flow rate of the fluid supply system falls below the flow rate threshold for the predetermined amount of time.

5. The method of claim 4 wherein the flow rate threshold is 5 mL/min and the predetermined amount of time is 15 seconds.

6. The method of claim 1, wherein the flow rate threshold is 5 mL/min, the predetermined amount of time is 15 seconds, and the integrity testing time period is 60 seconds.

7. The method of claim 1 wherein the one or more sensors comprise infrared sensors.

8. The method of claim 1 wherein the one or more sensors comprise contact sensors.

9. The method of claim 1 wherein the one or more sensors comprise magnetic sensors.

10. The method of claim 1 wherein the one or more sensors comprise ion sensors.

11. The method of claim 1 wherein the pressure source is pressurized to 55 mmHg.

12. The method of claim 1 wherein a pressure in a uterine cavity of the uterus is independent of a patient height relative to the pressure source.

13. A uterine treatment device, comprising:
    a shaft sized and configured for insertion into a uterus of a patient;
    an inflow lumen disposed along a length of the shaft;
    an outflow lumen disposed along the length of the shaft;
    at least one inflow port disposed at a distal end of the inflow lumen;
    at least one outflow port disposed at a distal end of the outflow lumen;
    a fluid reservoir operatively coupled to the inflow lumen and the outflow lumen;
    one or more sensors configured to measure a level of an air-fluid interface within the fluid reservoir;
    a fluid supply system connected to the fluid reservoir, the fluid supply system being configured to deliver fluid into the fluid reservoir;
    a pressure source connected to the fluid reservoir, the pressure source being configured to pressurize fluid in the fluid reservoir to deliver fluid from the fluid reservoir into the uterus of the patient;
    a pressure regulator disposed between the pressure source and the fluid reservoir, the pressure regulator being configured to reduce a pressure from the pressure source to a predetermined pressure value; and a controller configured to activate the fluid supply system to deliver fluid into the fluid reservoir, deactivate the fluid supply system when the level of the air-fluid interface within the fluid reservoir reaches an upper threshold, and re-activate the fluid supply system when the level of the air-fluid interface within the fluid reservoir reaches a lower threshold, the controller being further configured to determine that there is a leak in the uterus when a flow rate of the fluid supply system does not remain below a flow rate threshold for a predetermined amount of time over the course of an integrity testing time period.

14. The device of claim 13, wherein the controller is configured to determine that there is not any leak in the uterus when the flow rate of the fluid supply system falls below the flow rate threshold for the predetermined amount of time.

15. The device of claim 14, wherein the flow rate threshold is 5 mL/min and the predetermined amount of time is 15 seconds.

16. The device of claim 13, wherein the flow rate threshold is 5 mL/min, the predetermined amount of time is 15 seconds, and the integrity testing time period is 60 seconds.

* * * * *

UNITED STATES PATENT AND TRADEMARK OFFICE
CERTIFICATE OF CORRECTION

PATENT NO. : 11,331,037 B2
APPLICATION NO. : 16/077542
DATED : May 17, 2022
INVENTOR(S) : Robert Bilgor Peliks et al.

Page 1 of 1

It is certified that error appears in the above-identified patent and that said Letters Patent is hereby corrected as shown below:

In the Specification

Column 1
Lines 8-15, delete "This application claims the benefit under 35 U.S.C. 119 of U.S. Provisional Patent Application No. 62/297,643, filed February 19, 2016, titled "Methods and Apparatus for Determining the Integrity of a Bodily Cavity", and is a continuation-in-part of U.S. Patent Application No. 13/648,132, filed October 9, 2012, titled "Integrity Testing Method and Apparatus for Delivering Vapor to the Uterus", both of which are incorporated herein by reference." and insert -- This application is a National Stage of Application under 35 U.S.C. §371 and claims the benefit of International Application No. PCT/US2017/018729, filed February 21, 2017, which, claims priority to U.S. Provisional Patent Application No. 62/297,643, filed February 19, 2016. The entire contents of each of these priority applications are incorporated herein by reference. --

Signed and Sealed this
Twenty-eighth Day of June, 2022

Katherine Kelly Vidal
*Director of the United States Patent and Trademark Office*